US011253475B2

(12) United States Patent
Bleier

(10) Patent No.: US 11,253,475 B2
(45) Date of Patent: *Feb. 22, 2022

(54) PERIODONTIC TREATMENT AND METHOD

(71) Applicant: Cutting Edge Technology, LLC, Endicott, NY (US)

(72) Inventor: Larry P. Bleier, Endicott, NY (US)

(73) Assignee: Cutting Edge Technology, LLC

( * ) Notice: Subject to any disclaimer, the term of this patent is extended or adjusted under 35 U.S.C. 154(b) by 0 days.

This patent is subject to a terminal disclaimer.

(21) Appl. No.: 17/386,948

(22) Filed: Jul. 28, 2021

(65) Prior Publication Data

US 2021/0353541 A1    Nov. 18, 2021

Related U.S. Application Data

(63) Continuation of application No. 16/804,178, filed on Feb. 28, 2020, now Pat. No. 11,110,058, which is a continuation of application No. 15/355,185, filed on Nov. 18, 2016, now abandoned.

(51) Int. Cl.
*A61K 31/327*    (2006.01)
*A61K 31/65*    (2006.01)
*A61C 5/42*    (2017.01)
*A61P 1/02*    (2006.01)
*A61K 9/08*    (2006.01)
*A61K 9/00*    (2006.01)
*A61K 9/06*    (2006.01)
*A61C 5/40*    (2017.01)

(52) U.S. Cl.
CPC .................. *A61K 9/08* (2013.01); *A61C 5/40* (2017.02); *A61C 5/42* (2017.02); *A61K 9/0063* (2013.01); *A61K 9/06* (2013.01); *A61K 31/327* (2013.01); *A61K 31/65* (2013.01); *A61P 1/02* (2018.01)

(58) Field of Classification Search
CPC ........ A61K 31/327; A61K 31/65; A61C 5/42; A61P 1/02
See application file for complete search history.

(56) References Cited

U.S. PATENT DOCUMENTS

| | | | |
|---|---|---|---|
| 4,116,239 A | 9/1978 | Ewen | |
| 4,522,805 A | 6/1985 | Gordon | |
| 4,731,019 A | 3/1988 | Martin | |
| 4,820,152 A | 4/1989 | Warrin et al. | |
| 4,971,782 A | 11/1990 | Rudy et al. | |
| 4,980,152 A | 12/1990 | Frazier et al. | |
| 5,129,824 A | 7/1992 | Keller | |
| 5,330,357 A | 7/1994 | Keller | |
| 5,419,703 A | 5/1995 | Warrin et al. | |
| 5,985,249 A | 11/1999 | Fischer | |
| 6,074,293 A | 6/2000 | Bleier | |
| 6,183,251 B1 | 2/2001 | Fischer | |
| 6,361,408 B1 | 3/2002 | Bleier | |
| 6,949,018 B2 | 9/2005 | Bleier | |
| 6,960,615 B2 | 11/2005 | Glassman et al. | |
| 6,966,773 B2 | 11/2005 | Keller | |
| 8,956,161 B2 | 2/2015 | Keller | |
| 9,339,453 B2 | 5/2016 | King et al. | |
| 2003/0180229 A1 | 9/2003 | Kosli | |
| 2004/0253193 A1 | 12/2004 | Bosy et al. | |
| 2007/0287687 A1 | 12/2007 | Primus et al. | |
| 2010/0112525 A1 | 5/2010 | Keller | |
| 2011/0229841 A1 | 9/2011 | Hamada | |
| 2015/0352023 A1 | 12/2015 | Berg et al. | |
| 2018/0140379 A1 | 5/2018 | Bleier | |
| 2019/0142701 A1 | 5/2019 | Bleier | |

FOREIGN PATENT DOCUMENTS

| | | |
|---|---|---|
| WO | 2005027990 | 3/2005 |
| WO | 2011007217 | 1/2011 |
| WO | 2016014948 | 1/2016 |
| WO | 2018094154 | 5/2018 |

OTHER PUBLICATIONS

Wikesjo et al. "A biochemical approach to periodontal regeneration—Tetacycline treatment conditions dentine surfaces", Journal of Periodontic Research, 1986, 21: 322-329, Wiley.
Caton et al "A new classification scheme for periodontal and peri-implant diseases and conditions—Introduction and key changes from the 1999 classification" Journal of Clinical Periodontology, 2018, 45: (Supp 20) S1-8, Wiley.
American Board of Periodontology "American Academy of Periodontology Releases Proceedings from the 2017 World Workshop on the Classification of Periodontal and Peri-Implant Diseases and Conditions" Perio.org, Jun. 21, 2018.
Linares et al "Antibiotics as intermicrobial signaling agents instead of weapons", Proceedings of the National Academy of Science U.S.A., Dec. 19, 2006; 103(51): 19484-19489,.
Galler "Atridox(tm) A Valuable, Site-Specific Adjunct to Periodontal Therapy" https://www.oralhealthgroup.com/features/atridox-tm-a-valuable-site-specific-adjunct-to-periodontal-therapy/; Oct. 1, 2005.
Veerachamy "Bacterial adherence and biofilm formation on medical implants" a review, Proceedings of the Institution of Mechanical Engineers, Oct. 2014 228(10): 1083-99.
Wikipedia "Chitosan" https://en.m.wikipedia.org/wiki/Chitosan, retrieved Feb. 3, 2019.
Lozeau et al. "Effectiveness of a surface-bound antimicrobial peptide as a function of tether length", 2014 40th Annual Northeast Bioengineering Conference, Apr. 25-27, 2014 IEEE.

(Continued)

*Primary Examiner* — Jeffrey S Lundgren
*Assistant Examiner* — Chris E Simmons
(74) *Attorney, Agent, or Firm* — Goldstein Law Offices, P.C.

(57) ABSTRACT

Dental treatments and methods, including treating gum disease, using peroxide gel and a viscous antibacterial agent including tetracycline to chemically debride and curettage a treatment area. Treatments and methods include non-surgically scaling and root plaining the treatment area with dental tools such as periodontal scalers and/or curettes during the active period of the chemical debridement. The working surfaces of dental tools can be sharpened for optimal root and tooth surfacing during treatment. Treatment can include instructions for co-therapy by or on behalf of treatment subjects between visits and for maintenance care.

15 Claims, 5 Drawing Sheets

(56) References Cited

OTHER PUBLICATIONS

Lamster "Evaluation of components of gingival crevicular fluid as diagnostic tests", Annals of Periodontology, Mar. 1997; 2(1): 123-37, Wiley.
Hickok et al "Immobilized antibiotics to prevent orthopedic implant infections", Advances in Drug Delivery Reviews, Sep. 2012, 64(12): 1165-1176, Elsevier Science.
Arruda et al "Infection Control in Teeth with Apical Periodontitis Using a Triple Antibiotic Solution or Calcium Hydroxide with Chlorhexidine: A Randomized Clinical Study", Journal of Endodontics, Oct. 2018, 44(10) 1474-1479, Elsevier Science.
Pasternak et al "Metalloproteinases and their inhibitors—diagnostic and therapeutic opportunities in orthopedics", Acta Orthopaedica, Dec. 4, 2009; 80(6): 693-703, Taylor and Francis.
Moody "Microbial co-culture-harnessing internicrobial signaling for the production of novel antimicrobials" Future Microbiology 2014 9(5) 575-578, Future Medicine Ltd.
"Morbidity medical definition" Definition of Morbidity—NCI Dictionary of Cancer Terms, https://www.cancer.gov/publications/dictionaries/cancer-terms/def/morbidity.
Kim et al "Oral antibiotic treatment of staphylococcal bone and joint infections in adults", Journal of Antimicrobial Chemotherapy, 2014, 69:309-322, Oxford University Press.
Brooks et al "Six three-rooted premolars", The New York State Dental Journal, Nov. 2018, pp. 22-25.
Carrilho "Substantivity of Chlorhexidine to Human Dentin", Dental Materials, Aug. 2010, 26(8), pp. 779-785, Elsevier.
Kapoor et al "Systemic antibiotic therapy in periodontics", Dental Research Journal, Sep.-Oct. 2012 9(5): 505-515, Wolters-Kluwer.
Hickok et al. "Tethered Antibiotics", https://www.researchgate.net/publication/286110343_Tethered_Antibiotics/amp; retrieved Feb. 3, 2019.
DeStefano "The consequences of dull dental hygiene instruments on practice productivity", RDH, The National Magazine for Dental Hygiene Professionals, Sep. 1, 2018 pp. 1-9, PennWell Corporation.
Rottman et al "Titanium-Tethered Vancomycin Prevents Resistance to Rifampicin in *Staphylococcus aureus* in vitro", PLOS One, Dec. 2012, vol. 7, Issue 12 pp. 1-6.
Cappuyns "Viruses in periodontal disease—a review", Oral Diseases, Jul. 2005, 11(4) 219-229, Wiley.
International Preliminary Report on Patentabiligy for the corresponding international application PCT/US2017/062184, 13 pages, dated May 21, 2019.
Gordon et al "Tetracycline: Levels Achievable in Gingival Crevice Fluid and in Vitro Effect on Subgingival Organism: Part I. Concentrations in Crevicular Fluid After Repeated Doses." Journal of Periodontology, Oct. 1, 2018 (52)10 609 Wiley.
Temple University "Oral Microbiology Testing Service (OMTS) Laboratory", https://dentistry.temple.edu/aboratories-centers/oral-microbiology-testing-service-laboratory, retrieved Feb. 3, 2019.
Al-Rifaiy "The Effect of Mechanical and Chemical Polishing Techniques on the Surface Roughness of Denture Base Acrylic Resins", The Saudi Dental Journal, Dec. 24, 2009, vol. 22, pp. 13-17, Elsevier.
Salmeri "What is a Deep Cleaning or Scaling?" Dynamic Dental, Inc., blog.http://www.dynamicdentalinc.com/blog/bid/45863/What-is-a-deep-cleaning-or-scaling. Last accessed Jan. 11, 2018, p. 1, p. 1.
International Written Opinion for the corresponding application PCT/US17/62184, dated Jan. 30, 2018, 12 pages.
International Search Report for the corresponding application PCT/US17/62184, dated Jan. 30, 2018, 3 pages.
"American Academy of Periodontology Statement on Local Delivery of Sustained or Controlled Release Antimicrobials as Adjunctive Therapy in the Treatment of Periodontitis", American Academy of Periodontology, May 2006, pp. 1458, vol. 77, No. 8, USA.
Bhardwaj et al., Effect of Tetracycline Hydrochloride as Root Conditioner: A Scanning Electron Microscopic Study, Lambert Academic Publishing, 2012 pp. 1-58, LAP Lambert Academic Publishing GmbH & Co. KG, Saarbrucken, Germany.
Burgers et al., "In Vivo and In Vitro Biofilm Formation on Two Different Titanium Implant Surfaces", Clin Oral Implants Res, Feb. 2, 2010, pp. 156.
Cochrane et al., "Case Series Report of 66 Refractory Maintenance Patients Evaluating the Effectiveness of Topical Oxidizing Agents"; The Journal of Clinical Dentistry, 2015, pp. 109-114, vol. 26, No. 4, USA.
Cohen et al., "Position Paper: Periodontal Maintenance", Journal of Periodontology, 2003, pp. 1395-1401, vol. 74, No. 9, USA.
Dominguez-Moreira et al., "Gingival Bleeding Reduction Using a Carbamide Peroxide Based Tooth Paste with Lactoperoxidase", Journal of Clinical and Experimental Dentistry, 2011, pp. 452-455, vol. 3, No. 5, Spain.
"Gly-oxide Liquid", Drugs.com, Jan. 31, 2011, http://www.drugs.com/drp/gly-oxide-liquid.html, Nov. 22, 2016.
Keller, "Minimizing Bacteremia in Periodontal Disease Treatment", The American Academy for Oral Systemic Health, Apr. 9, 2011, pp. 1-6.
Lazarchilk et al., "Use of tray-applied 10 percent carbamide peroxide gels for improving oral health in patients with special-care need", JADA, Jun. 2010, pp. 639-646, vol. 141, No. 6, American Dental Association.
Leknes et al., "Influence of tooth instrumentation roughness on subgingival microbial colonization", Journal of Periodontology, Apr. 1994, pp. 303, vol. 65, No. 4.
Nanda et al., "Root conditioning in periodontology—Revisited", Journal of Natural Science, Biology and Medicine, Jul.-Dec. 2014, pp. 356-358, vol. 5, No. 2, Journal of Natural Science, Biology and Medicine.
Pandit et al., "Comparative evaluation of locally delivered minocyclien and metronidazole in the treatment of periodontitis", Contemporary Clinical Dentistry, Jan.-Mar. 2013, pp. 48-53, vol. 4, No. 1, Medknow Publications.
Paquette et al., "The Sharpening of Scaling Instruments: 1. An Examination of Principles", Journal of Periodontology, Mar. 1977, pp. 163-168, vol. No. 48. No. 3, Journal of Periodontology.
Perayil et al., "Comparison of the efficacy of subgingival irrigation with 2% povidone-iodine and tetracycline HCl in subjects with chronic moderate periodontitis: A clinico microbiological study", Dental Research Journal, Mar.-Apr. 2016, pp. 98-109, vol. 13, No. 2, Midknow Publications.
Perioperspectives: Our Academy. Our Community, Jul.-Sep. 2015, pp. 1-52, American Academy of Periodontology.
Quirynen et al. "The influence of surface roughness and surface-free energy on supra-and subgingival plaque formation in man. A review of the literature", Journal of Clinical Periodontology, Jan. 1995, pp. 1-14 (summary page only), vol. 22, No. 1 PubMed.
Rossi et al., "A Scanning Electron Microscope Study Comparing the Effectiveness of Different Types of Sharpening Stones and Curets", Journal of Periodontology, Nov. 1995, pp. 956, vol. 66.
Schaudinn et al., "Periodontitis: an archetypical biofilm disease", Journal of American Dental Association, Aug. 2009, pp. 2, Pubmed.
Slots, Jorgen, "Selection of antimicrobial agents in periodontal therapy", Journal of Periodontal Research, 2002, pp. 389-398, vol. 37, Blackwell Munksgaard Ltd. United Kingdom.
Subramani et al., "Biofilm on dental implants: a review of the literature", The International Journal or Oral & Maxillofacial Implants, Jul.-Aug. 2009, pp. 616, vol. 24, No. 4, PubMed.
Sundfeld et al., "Treatment of Enamel Surfaces After Bracket Debonding: Case reports and Long-term Follow-ups"; Journal of Operative Dentistry, Jan.-Feb. 2016, pp. 1 (summary only), Pubmed.
Smiley et al. "Systematic Review and Meta-Analysis on the Non-surgical Treatment of Chronic Periodontitis by Scaling and Root Planing with or without Adjuncts", ADA Center for Evidence-Based Dentistry, Jul. 2015, pp. 1-179.
Tariq et al, "Treatment modalities and evaluation models for periodontitis", Jul.-Sep. 2012; pp. 106-122, vol. 2, No. 3, Medknow Publications.

(56) References Cited

OTHER PUBLICATIONS

Teughels et al., "Effect of material characteristics and/or surface topography on biofilm development", Clinical Oral Implants research, Oct. 2006, pp. 68-81 (summary only), vol. 17, Suppl. 2.

"Statement on the Safety and Effectiveness of Tooth Whitening Products", American Dental Association, Sep. 2, 2014, pp. 1-4, https://web.archive.org/web/20140902095043/http://www.ada.org/ . . . .

"Trilogy Professional Cleansing & Care Debriding Serum", Trilogy, 2015, pp. 1-12, NOWsystem, Inc.

Unsal et al., "Influence of a single application of subgingival chlorhexidine gel or tetracycline paste on the clinical parameters of adult periodontitis patients", Journal of Clinical Periodontology, May 1994, pp. 351-355, vol. 21, No. 5, Wiley Online Library.

Yao et al., "In vitro antibacterial effect of carbamide peroxide on oral biofilm", Journal of Oral Microbiology, Jun. 12, 2013, pp. 1-7, Co-Action Publishing.

Zia et al, "Endodontic irrigantasarootconditioningagent" An in vitro scanning electron microscopic study evaluating the ability of MTAD to remove smear layer from periodontally affected root surfaces, Singapore Dental Journal, 2014, vol. 35, pp. 1-52, Elsevier B.V.

PERIODONTIC TREATMENT AND METHOD

CROSS REFERENCE TO RELATED APPLICATIONS

This application is a continuation of U.S. patent application Ser. No. 16/804,178, filed on Feb. 28, 2020, which is a continuation of U.S. patent application Ser. No. 15/355,185, filed on Nov. 18, 2016, which is relied upon and incorporated herein by reference in its entirety. The entire disclosure of any publication or patent document mentioned herein is entirely incorporated by reference.

TECHNICAL FIELD

The present disclosure relates generally to methods of treating periodontal disease. More particularly, the present disclosure related to a method of root conditioning a periodontitis-affected tooth of a subject having a root surface and a periodontal pocket.

BACKGROUND

Within minutes after a tooth surface has been thoroughly cleaned, bacterial plaque initiation begins. To control this continuous colonization and maturation of the bacterial plaque, and eventually calculus deposition as well, one must adhere to a basic oral hygiene regimen. This regimen usually consisted of basic tooth brushing and flossing.

Periodontitis is an inflammatory condition of the supporting dental tissues that is normally treated by mechanical removal of the subgingival and supragingival biofilm. This traditional mechanical treatment generally known as scaling and root planing, is not entirely effective, but remains the "gold standard" for the non-surgical management of chronic periodontitis. Currently, the most widely accepted definitions of scaling and root planing are:
1. Scaling involves instrumentation of the crown and root surfaces of the teeth to remove plaque and calculus from these tooth surfaces. This definition of scaling was published Aug. 29, 2016 by the American Dental Association releases guideline on gum disease treatment dates Jul. 1, 2015.
2. Root planing is the definitive procedure designed for the removal of cementum and dentin that is rough and/or permeated by calculus or contaminated with toxins or microorganisms.
This mechanical therapy may, however, fail to reduce or eliminate the anaerobic infection at the base of the pocket, within the gingival tissues or in furcations of multirooted teeth. Some of the periodontal pathogens have been studied and found to travel into lacunar defects in the cementum, which further extend into exposed radicular dentin. These have been reported to act as bacterial reservoirs from which recolonization of mechanically treated root surfaces can occur. The bacterial reservoirs not eliminated by conventional periodontal therapy can further be suppressed with various adjunctive therapies that have been investigated to improve the clinical outcome, namely, with the use of chemotherapeutic agents. Various locally delivered chemotherapeutic agents available are: Tetracycline fibers, metronidazole gel, minocycline ointment and minocycline microspheres, chlorhexidine chip, doxycycline hyclate, sodium bicarbonate and 3% hydrogen peroxide, antimicrobial toothpastes, mouth washes like Listerine, chlorhexidine, sanguinaria, non-steroidal anti-inflammatory agents, irrigation, and lasers. Therefore, the bacterial reservoirs not eliminated by the incomplete conventional mechanical therapy of root planing instrumentation can be further suppressed with the use of chemotherapeutic agents.

The tetracycline group of antibiotics are among the most commonly used active agents for the treatment of periodontitis as they are active against periodontopathic microorganisms, and they offer better resorption, protein binding diffusion into tissue structure and anti-collagenase properties. High degree substantivity of the drugs and agents allow for controlling of microbial plaque. Conventionally such antibiotics are administered after treatment via ingestion (e.g., via prescription tablets or capsules).

For decades, localized antimicrobial therapy, in particular, has evoked growing interest because of the site-specific nature of periodontal infections, the possible higher concentration of an anti-microbial agent subgingivally together with the reduced side-effects of systemic antibiotic use, as well as the acceptance that most clinicians lack the skills for proper periodontal therapy root planing and scaling instrumentation to achieve reliable periodontal health alone with just a mechanical approach.

Of course, it is well known how difficult hand instrumentation is to perform. For example, cavitrons and other sonic instrumentation approaches have been found to remove only approximately 50% of the calculus and surface roughness of tooth surfaces, even when scaling and root planing extracted teeth outside the oral cavity.

Dental care professionals in private practice also often have inadequate skills or time to sharpen dental scalers and curettes prior to treating each and every patient. The clinicians performing these procedures mostly do so with one treatment visit and only one attempt at scaling and root planing for each tooth, whether by doing one quadrant treatment visit or up to four quadrants at one visit. Busy full hygiene work schedules and the financial demands and needs of the dental office prohibit them from checking every instrument for sharpness for proper root planing and scaling before each patient and during the treatment without retesting for sharpness as the instruments are used. Instruments become dull even during the same treatment as it is used throughout the mouth. Some of this treatment decision making is dictated by insurance company plans paying for reimbursement on a one quadrant-per-visit basis, and will not supplement additional payment if the same quadrant is treated over multiple visits. Some hygienists have gone as far as to point out that they sharpen their instrument one or twice a year or rely on sonic and ultrasonic instrumentation, which also has limitations.

Further, manual scaling and root planning can often be difficult and time consuming due to the complex and unfavorable root morphology when working blindly at deep pocket sites. Several studies have supported the gains that root planning can reduce probing depths, gain clinical attachment and help inhibit disease progression. Scaling and root planing is a localized treatment but is not able to get rid of the pathogenic bacteria at all times due to their presence within periodontal tissues, or in the case of deeper pockets, where the instruments are difficult to reach. As probing depth increases, manual instruments become less efficient to confiscate the root of the problem especially with compromised unfinished cutting edges provided by the various manufacturers and are not refined and maintained by the clinician. Research indicates that the cutting edges on most instruments become dull with deformations in the cutting edges by 15 to 30 strokes on the roots of teeth. In addition, several studies have also reported that the microbiological and clinical effects achieved by ultrasonic debridement that can aid in root planing and scaling are similar to those achieved by manual scaling and root planing alone. Interestingly, hygiene schools teach students ultrasonic and sonic instrumentation to protect the clinician hygienist from work injuries such as carpal tunnel and other wrist job-related injuries, often to the detriment of the patient.

Under ideal conditions of research, after mechanical debridement, the microbial load drops to 0.1%. However, microbial bacteria recolonize within a week's time with less pathogenic composition. In this perspective, the concept of one stage full-mouth disinfection was introduced in 1995 for the avoidance of re-infection from microbial reservoirs and this approach still shows promise. Bacteria thus remain the foremost etiological factor responsible for periodontal disease, and therefore the use of antimicrobial therapy along with the mechanical therapy is a good biological rational for the treatment of the periodontal disease. In the later more advanced stages of periodontal disease, with deeper pockets, the clinician has to be aware of different treatment strategies and various approaches including surgical intervention that still includes mechanical therapy and possible use of pharmacological agents. Medications are specifically used for better management of periodontitis and include antimicrobials that change the microbial flora sufficiently along with host modulating agents which modify the host response like reduction of excessive destructive enzymes levels, cytokines, prostaglandins and osteoclastic activities. The clinician relying on non-surgical therapy approaches should therefore have a good understanding of different techniques of soft tissue management, and the re-evaluation of the endpoint for non-surgical therapy, and, the preparation and timing for periodontal surgical intervention which can include for example, tissue re-attachment, respective, plastic and regenerative techniques. Other surgical techniques address and help manage the apical migration of the periodontal attachment apparatus from gingival recession and other mucogingival pathology which can include frenectomy, free gingival, pedicle and connective tissue grafting among other techniques too numerous to mention here.

As will be appreciated, periodontal pockets are only one of many manifestations of periodontal disease with bacteria induced inflammation. The bacterial induced inflammation can combine with mechanical injuries such as tooth bushing injuries, trauma such as heat, viral and chemical injuries, atrogenic injuries such as a result of some orthodontic treatment, and developmental abnormalities that need to be addressed and treated as well. These injuries for example, cause periodontal attachment loss, including clinical findings of gingival recession and bone loss from root exposure; periodontal attachment loss with gingival recession root decay and root thermal and mechanical sensitivity can be substantial.

Periodontitis is an inflammatory disease caused primarily by the periodontal plaque bacteria, although the host immune responses also play an important role. With the advent of concept of delivery of systemic antibiotics, solutions have included intrapocket devices for the treatment of periodontitis for more physiologically acceptable and commercially feasible drug delivery systems as an adjunct to the conventional surgical and nonsurgical treatments for periodontal infections.

For example, U.S. Pat. No. 8,956,161 entitled Article and Method for Controlling Oral-Originated Systemic Disease, the entirety of which is incorporated by reference hereby, describes a method for treating periodontitis by administering a 1.7% hydrogen peroxide gel using a "Perio-Tray™"— noting that oral rinses and gels can treat gum disease, but cannot effectively treat periodontal pockets without the specialized delivery tray because rinses, brushing and flossing "do not typically penetrate greater than 3 mm into the periodontal pocket" and "medicament applications into the periodontal pocket are unable to maintain a modified environment sufficient for health and healing." The adjunctive use over three months of 1.7% hydrogen peroxide gel, locally administered using prescription customized trays in the treatment of subjects with moderate to advanced periodontitis, demonstrated statistically significant clinical improvements in pocket depths and bleeding when compared with scaling and root planning alone. Putt M S, Proskin H M. *Custom tray application of peroxide gel as an adjunct to scaling and root planing in the treatment of periodontitis: a randomized, controlled three-month clinical trial*. J Clin Dent. 2012; 23(2):48-56. PubMed. PMID: 22779217.

A recent systematic extensive review article was recently published on the current published literature with meta-analysis on the nonsurgical treatment of chronic periodontitis by scaling and root planing with or with adjuncts by an extensive search of PubMed/MEDLINE and Embase for randomized controlled trials of scaling and root planing with or without the use of adjunctive treatments with clinical attachment level (CAL) outcomes of trials at least six months in duration by the ADA Center for Evidence-Based Dentistry, dated July 2015. The conclusions of the review of 72 articles was that randomized controlled trials of SRP versus no treatment or debridement is scant, but confirmed the commonly reported result of approximately 0.5 mm improvement in CAL (clinical attachment levels). The literature on adjunctive therapies up to now was varied providing only a moderate level of certainty on the benefits of the four systemic adjunctive therapies: systemic sub-antimicrobial dose doxycycline, systemic antimicrobials, chlorhexidine chips, and photodynamic therapy with a diode laser. There was a low level of certainty on the benefits of all other adjunctive therapies.

SUMMARY

The ultimate goal of periodontal therapy is to preserve or maintain the dentition in a state of health and comfort throughout life of the individual. Ideally, periodontal therapy should eliminate inflammation, arrest progression of periodontal disease, improve aesthetics and create an environment conducive to the maintenance of health. The need for effective prevention, control and treatment and preventative maintenance of periodontal diseases is growing. The patient should be looked upon as a co-therapist who values being enabled to play a more active role in self-treatment, rather than always relying on a clinician. The prevalence of periodontal attachment loss increases with age. 50 percent of 18- to 19-year old subjects; about 80 percent of 35- to 39-year old subjects; 87 percent for 45 to 49 years; and exceeded 90 percent for those 60 years and older. Most cases can be successfully treated by nonsurgical periodontal therapy (Phase I and Phase III). The vast majority of periodontal treatment needs should be addressed to early detection by treating gingivitis and early periodontitis, preventing disease progression and maintaining periodontal health, following active periodontal therapy. Therapeutic scaling and root planing is performed to treat established periodontal disease at various levels found throughout the individual's dentition and treatment decisions should be site specific for each tooth.

According to at least one of the various embodiments, disclosed is a method for treating periodontal disease comprising: administering a gel solution including a clinically effective amount of a peroxide to a periodontal pocket of a subject in conjunction with a mechanical debridement treatment, wherein the peroxide when applied chemically debrides and anesthetizes the treatment area associated with the periodontal pocket; and administering a viscous antibacterial agent comprising a clinically effective amount of tetracycline to the periodontal pocket of the subject in conjunction with the mechanical debridement treatment. In at least one of the various embodiments, the gel solution can comprise at least 10% carbamide peroxide. In at least one of the various embodiments the viscous antibacterial agent can consists essentially of a tetracycline.

The broad definition of mechanical debridement can include tools and devices beyond hand instrumentation with dental scalers and curettes such as sonic and ultrasonic scalers, lasers and other devices that can alter the surface physical properties both organic and inorganic of implants and tooth root surfaces for optimized controlled surface finishing. Blades and other functional cutting edges of the instrument can include any cutting edges or working edges, for example, sonic or ultrasonic tip(s) or laser tip(s).

In at least one of the various embodiments the gel solution, the viscous antibacterial agent or both can be applied to a subject at a pocket depth of 5 or more millimeters in conjunction with a non-surgical mechanical debridement periodontal disease treatment. In at least one of the various embodiments, the periodontal pocket depth can be at least 7 millimeters. In at least one of the various embodiments, the periodontal pocket depth can be at least 10 millimeters.

In at least one of the various embodiments, the 10% carbamide peroxide gel solution can be used as an anesthetic in an amount effective amount forestall the need for another anesthetic.

In at least one of various embodiments the viscous antibacterial agent can be a tetracycline powder, wherein the tetracycline powder becomes viscous when administered.

In at least one of various embodiments the method can further comprise: sharpening or finishing a dental instrument working surface with a finishing tool; and performing the mechanical debridement with the sharpened or finished dental instrument. The finishing tool is configured to produce an optimized working surface of the blade such that the mechanical debridement treatment is executed with the optimized working surface. The sharpening tool can be configured to produce an optimized working surface including at least one of no wire edges and a surface sharpened from 1-5 microns.

In at least one of the various embodiments the method can further comprise: sharpening or finishing a dental instrument working surface with a finishing tool; and performing optimized surface finishing for dental implants with the sharpened or finished dental instruments. The finishing tool is configured to produce an optimized working surface of the blade or functional edge such that the implant surface finishing treatment is executed with the optimized working surface. The finishing tool can be configured to produce an optimized working surface for an instrument including, for example, no wire edges, no deformations, and/or a working surface finished to the tolerances of the implant.

In an embodiment, provided is a tool with an optimized working surface that can produce a controlled finished surface for an implant in vivo. For example, a finishing tool can be configured to retap or reshape the body of the implant which is in the bone. Finishing and shaping working surfaces can include surfaces for tap, tap die, plasma spray, burnishing, and thread cleaning. In an embodiment, the screw sharpening or shaping tool can be configured to be attached to an implant drill or implant remover wrench, for in vivo use.

In various embodiments, the instrument is finished to a controlled finished surface that is optimal for the use of the instrument. For example, an instrument for finishing bone for a bone graft can be finished to a roughness that encourages a successful graft (e.g. on the order of 100's of microns) for osteoplastic activity or osteocytes that respond to increased bone roughness. For another example, a finishing tool can be configured to shape an implant surface that is to be biologically clean to a finish that is smoother, for example 1-99 microns. Finishes can allow for the placement for sprayed or painted root conditioners.

As described herein, finishing tools can be used to produce an optimized working surface for a metal alloy, ceramic, or plastic of any manufactured instrument.

In at least one of the various embodiments, the method can include sharpening a dental blade with a sharpening tool configured to produce a cutting edge that optimizes the working surface of the blade, for example by optimizing the rake angle, such that the mechanical debridement treatment is executed with the optimized blade.

In at least one of the various embodiments the method can comprise: instructing the subject or the subject's caretaker to have the subject floss with the gel solution including the carbamide peroxide at least once daily for the active phase of the periodontal disease. In at least one of the various embodiments, the method can comprise: instructing the subject or the subject's caretaker to have the subject gumbrush with the gel solution including 10% carbamide peroxide at least once daily for the active phase of the periodontal disease after the treatment. In at least one of the various embodiments, the method can comprise: instructing the subject or the subject's caretaker to have the subject regularly floss with the solution including 10% carbamide peroxide at least once daily during a maintenance phase of the periodontal disease as a part of the subject's regular dental care routine after the treatment.

In at least one of the various embodiments, the method can comprise administering a first application of the viscous antibacterial agent prior to applying a first application of the gel solution.

In at least one of the various embodiments, the method can comprise: administering the viscous antibacterial agent, the gel solution or both a plurality of times during the active phase of the disease. In at least one of the various embodiments, the method can comprise: applying a follow up treatment comprising: administering the gel solution to the periodontal pocket of a subject; and administering the antibacterial agent to the periodontal pocket of a subject.

In at least one of the various embodiments, disclosed is a dental treatment method comprising: administering a gel solution including a clinically effective amount of peroxide to a treatment area of a subject in conjunction with a mechanical dental care treatment, wherein the peroxide solution chemically debrides and anesthetizes the treatment area; and administering a viscous antibacterial agent comprising a clinically effective amount of tetracycline to the periodontal pocket of the subject during the dental care treatment.

In at least one of the various embodiments, the gel solution can comprise at least 10% carbamide peroxide. In at least one of the various embodiments the viscous antibacterial agent consists essentially of tetracycline. In at least one of the various embodiments, the dental care treatment can include a treatment selected from: treating a dental root for a bone graft, treating or preventing peri-implantitus, treating a dental surgery tissue transplant, and treating a root of the subject. In at least one of the various embodiments, the dental care treatment can comprise treating or preventing peri-implant mucositis and peri-implantitis from a titanium implant.

In at least one of the various embodiments, the dental care treatment can comprise treating the root of the subject by root plaining or root conditioning or both. In at least one of the various embodiments, the treating the root of the subject includes treating a root canal apical endodontic periodontic lesion, for example, during an apioectomy.

In at least one of the various embodiments, the dental care treatment method can comprise applying a follow up treatment comprising: administering the gel solution to the treatment area of a subject; and administering the viscous antibacterial agent to the treatment area of a subject.

In at least one of various embodiments the method can further comprise: sharpening or finishing a dental instrument working surface with a finishing tool; and performing the mechanical dental care treatment with the sharpened or finished dental instrument. The finishing tool can be configured to produce an optimized working surface of the blade such that the mechanical dental care treatment is executed with the optimized working surface. The sharpening tool can be configured to produce an optimized working surface including at least one of no wire edges, no deformations, of a surface sharpened from 1-5 microns, or creating an optimized controlled roughness or smoothness for better cellular tissue repair or cellular proliferation or enabling better controlled surface roughness for further chemical treatments and adhesion of "bonding agents" that need controlled surface pre-roughness at set micron levels.

In at least one of the various embodiments, the disclosure provides a viscous medicament composition comprising a first component including at least about 10% by weight of carbamide peroxide as an active agent; and a second component comprising an antibacterial agent. In an embodiment, the second component can consist essentially of tetracycline. In at least one of the various embodiments, the viscous medicament is a gel composition. In at least one of the various embodiments, the solution can comprise: the medicament comprising a weight percentage of the first component effective to chemically debride a treatment area for a dental treatment. In at least one of the various embodiments, the part percentage of the antibacterial agent consisting essentially of tetracycline is the remaining part of the solution.

In at least one of the various embodiments, described is a dental product comprising: a dental cleaning device coated, impregnated or provided with a solution including at least 10% carbamide peroxide. The dental cleaning device can be selected from the group consisting of: brushes and interdental cleaners. In at least one of the various embodiments, the interdental cleaning device can be selected from the group consisting of: flosses, picks, or interdental brushes. In at least one of the various embodiments, the interdental cleaning device is superfloss including a sponge provided with the at least 10% carbamide peroxide.

In at least one of the various embodiments, described is a method for treating periodontal disease comprising: administering a gel solution including peroxide gel and a viscous antibacterial agent comprising a clinically effective amount of tetracycline to a periodontal pocket of a subject with a periodontal probe or other dental instrument to chemically debride and curettage the treatment area; and non-surgically scaling and root plaining the treatment area with the periodontal scalers or curettes during the active period of the chemical debridement. The periodontal pocket treated can be at least 5 mm.

The method can further comprise: sharpening or finishing a dental instrument working surface with a finishing tool configured to produce an optimized working surface of the blade such that the root plaining treatment is an enhanced root planing, wherein the optimized working surface including at least one of no wire edges and a surface sharpened from 1-5 microns.

As used herein, "treating" or "treatment" means the prevention or reduction of severity of symptoms or effect of a disorder or disease and curative treatments therefor. A "subject" according to the invention refers to any multicellular organism having skin. Typically, the subject will be a mammal, such as a mouse, a rat, a pig, a horse, a cat, a dog, an elephant, a giraffe, a monkey, or a human, and the like. Typically, the mammal will be a human.

The term "administering" as used herein refers to any method which, in sound medical practice, delivers the composition to a subject in such a manner to so as to be effective in the treatment of a dental disorder. The compositions are preferably administered such that they cover the entire area to be treated.

The phrase "safe and effective amount" as used herein, means an amount of a composition or component thereof sufficient enough to positively modify the disorder to be treated but low enough to avoid serious side effects, within the scope of sound medical advice. Safe and effective amounts will vary with the particular disorder or disorders being treated, the severity of the disorder, the duration of the treatment, the specific components of the composition being used, and like factors as are known by health-care providers, including physicians and veterinarians.

As used herein, the term "enhanced root planing" means a treatment procedure designed to remove cementum or surface dentin that is rough, impregnated with calculus, or contaminated with toxins or microorganisms. In particular, enhanced root planing as described herein is the process by which residual embedded calculus and disease root cementum are removed from the tooth surface to produce a smooth, hard and biologically clean surface. This helps allow a patient's oral tissues, namely, the periodontal (gum) tissues, and supporting bone to repair and regenerate on the tooth root surfaces of the dentition. Disclosed are embodiments for enhanced root planing with dental instruments including refined functional optimized working surfaces. For example, described herein are dental instruments including smooth and sharp cutting edges configured specifically for dental procedures to create as close as possible a root surface smoothness. Root surface smoothness should, if possible, be similar to the white enamel of a tooth, kitchen glass or other smooth surface to minimize bacterial growth and help prevent repopulations of microorganisms on the root. Root surfaces are tested for smoothness with special instruments by the clinician after treatment.

In embodiments, enhanced root planing can also mean a treatment procedure that includes mechanical root planing together with chemical debridement using viscous chemical treatments and antibacterial agents, for example, a peroxide gel solution that chemically debrides a treatment area of the periodontium; and a viscous antibacterial agent including a clinically effective amount of a tetracycline. Viscous chemical treatments can include those provided in a viscous form, for example a peroxide gel including 10% carbamide peroxide, or chemical treatments that become viscous when administered for treatment, for example a tetracycline powder that forms a paste when administered by virtue of mixing with crevicular flow or another treatment (e.g. a peroxide gel).

BRIEF DESCRIPTION OF THE DRAWINGS

Embodiments are illustrated in the figures of the accompanying drawings, which are meant to be exemplary and not limiting, and in which like references are intended to refer to like or corresponding things.

DETAILED DESCRIPTION OF THE PREFERRED EMBODIMENTS

Gingival health is influenced by many local factors. Some specific local factors are bacterial plaque, and calculus. These local factors, in part, contribute to the gingiva's inflammatory response. Proper oral hygiene can control many of these local factors so that the disease process is never initiated or is reversed in cases where initiation has taken place. Untreated gingivitis, however, can lead to periodontitis.

Periodontitis is a severe infection of the gingiva which destroys the gingival tissue and bone that supports teeth. In a person with periodontitis, the inner layer of the gingiva and bone pull away from the teeth and form pockets. These pockets between the teeth and gums continue to collect debris and toxic substances as a result of the bacterial growth and bacterial maturation and infection. The body's immune system fights the bacteria as the plaque spreads and grows below the gum line. The toxins or poisons produced by the bacteria in plaque biofilm as well as enzymes produced by the body's natural immune response in fighting infection break down the bone and connective tissue that hold teeth in place. As the disease progresses, the pockets deepen and more gum tissue and bone are destroyed. When this happens, teeth are no longer anchored in place, they become loose, resulting in tooth loss. Periodontitis also disrupts a healthy bacteria and T-cell balance, destroys collagen production for connective tissue, and destroys the pocket wall. Periodontitis is further associated with an increased risk of heart attack, stroke, and other severe health problems.

Periodontitis falls into different classes: chronic periodontitis and aggressive periodontitis. Chronic periodontitis is most common and occurs mostly in adults with progression in severity over many years despite most cases showing signs of periodontal attachment loss as early as 18 years of age. Aggressive periodontitis is comparatively rare and occurs mostly during childhood or adolescence.

Figure 1A:
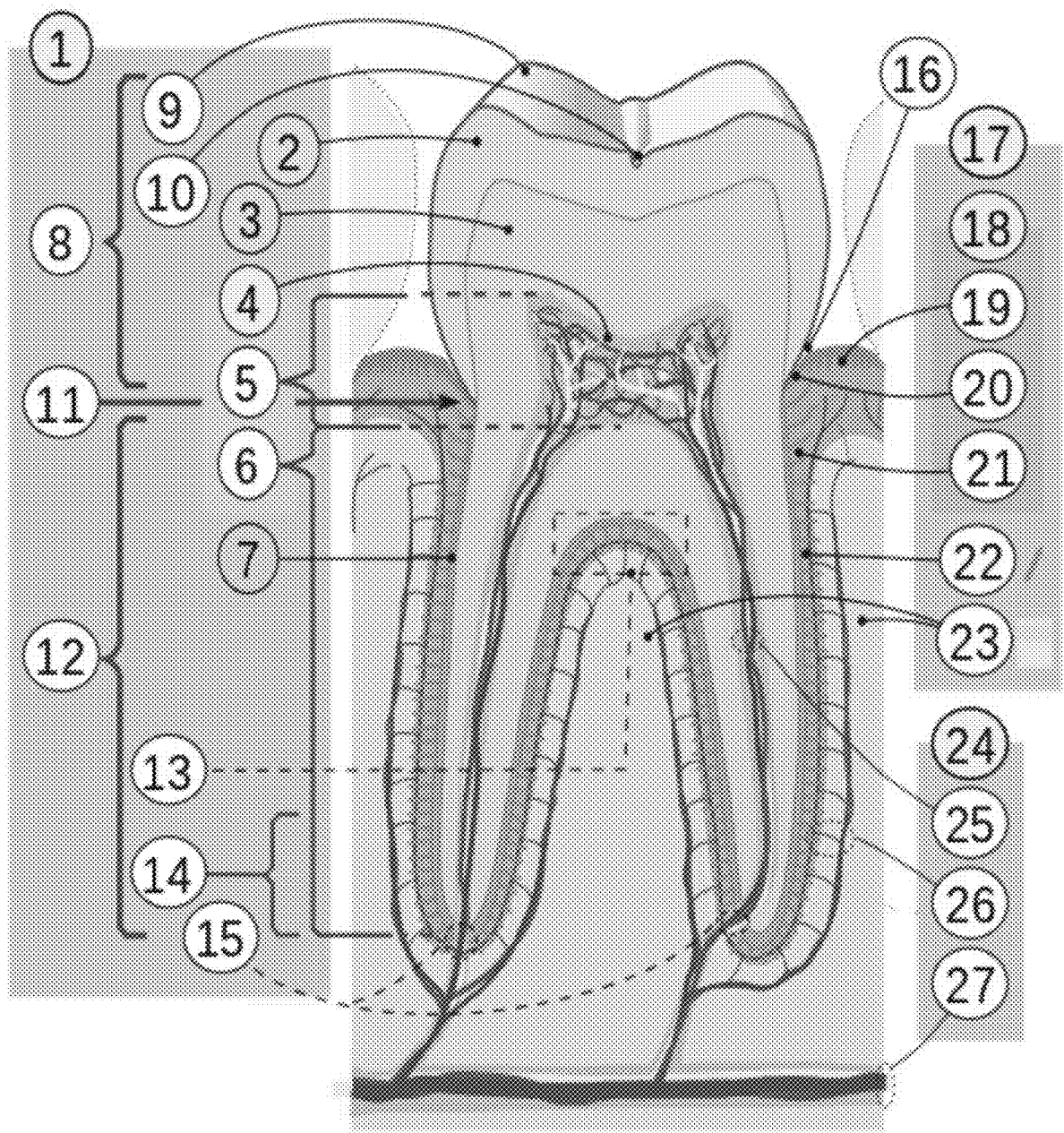
FIGS. 1A-1B illustrates a cross-section of a tooth in a healthy periodontium.
Figure 1B:
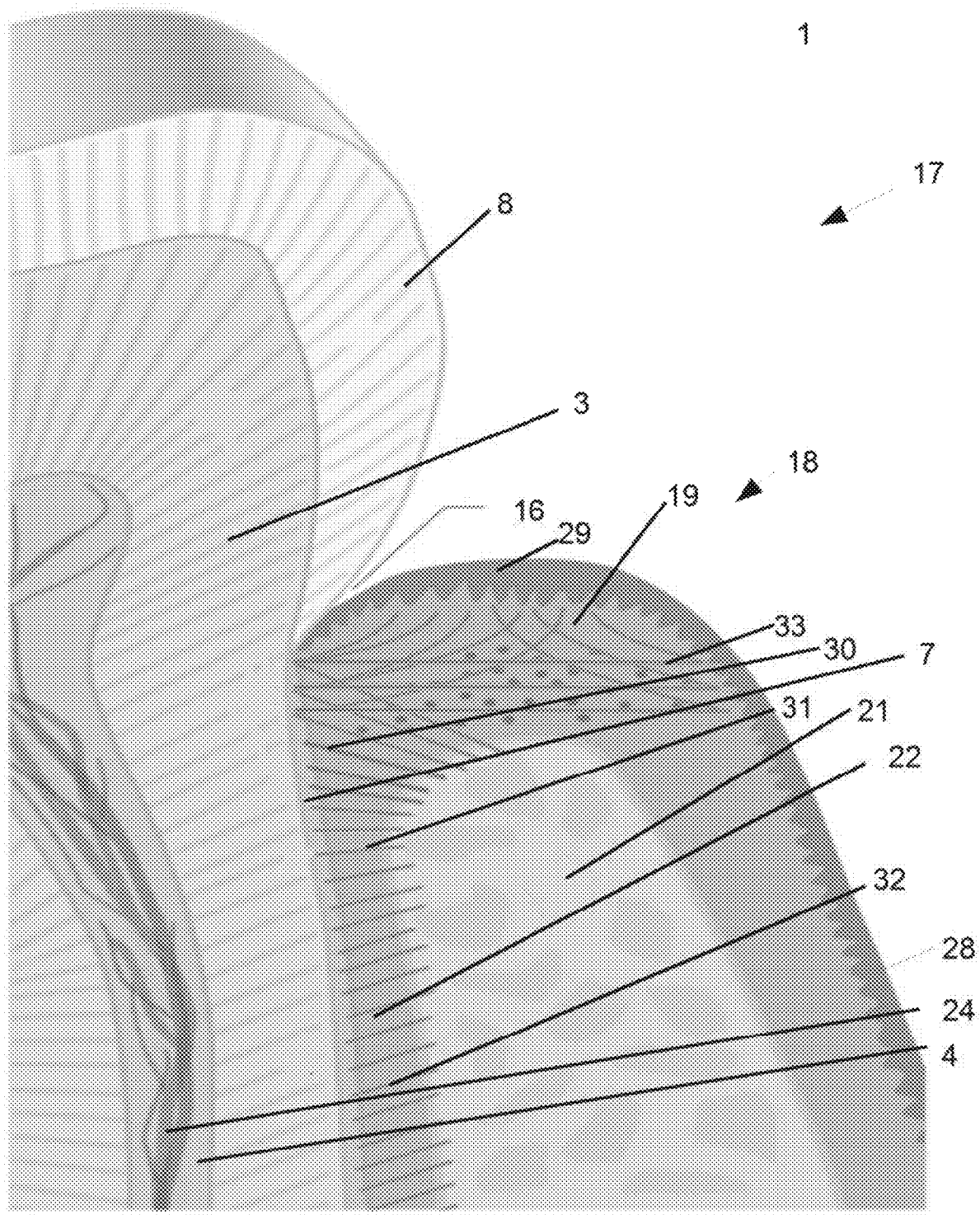

FIGS. 1A-1B show a cross section of a tooth 1 in a healthy periodontium 17. The crown 8 of each tooth 1 has a coating of enamel 2, which protects the underlying dentine 3. Enamel is the hardest substance in the human body, harder even than bone. It gains its hardness from tightly packed rows of calcium and phosphorus crystals within a protein matrix structure. Once the enamel has been formed during tooth development, there is little turnover of its minerals during life. Mature enamel is not considered to be a 'living' tissue. The top of the crown 8 is the cusp 9 of the tooth 1.

Dentine 3, a major component of the interior of the tooth 1, is a bone-like elastic and compressible live tissue which connects with a central neve within the dental pulp 4. The dental pulp includes cameral pulp 5 and root pulp of the root canal 6. The root canal 6 forms the central chamber of the tooth. The root pulp of the root canal 6 is made of soft tissue and contains dental blood vessels and nerves 25.

The root 12 is the region of the tooth 1 that is below the gum; the neck 11 is the area that divides the crown 8 from the root. Some teeth 1 have only one root, for example, incisors and canine ('eye') teeth, whereas molars and premolars have up to 4 roots per tooth. At the base of the root trunk of a multi-rooted tooth 1 is a furcation 13 where two or more roots meet. The extension of the root pulp 6 within the root 12 of the tooth 1 is called the root canal 6. The root canal 6 connects with the surrounding tissue via the apical foramen 15, an opening at the apex 14 of the root 12. This is an opening in the cementum 7 through which the tooth's 1 vessels and nerves 24 enter the dental pulp 4 from the surrounding tissue. The vessels supply and circulate blood delivered from the alveolar through channel 27.

The periodontium 17 refers to the supporting tissues of the teeth, including the alveolar bone 21, the gingiva 18, the periodontal ligament 22, and the outer layer of the tooth 1 roots 12, which are covered by a layer of cementum 7. The gingiva 18 is the only clinically visible component of the periodontium 17 inside the mouth.

The periodontal ligament 22 is a group of specialized connective tissue fibers that attach a tooth to the alveolar bone within which it sits. The periodontal ligament 22 consist of cells, and an extracellular compartment of fibers. The cells are fibroblast, epithelial cells, undifferentiated mesenchymal cells, bone and cementum cells. The extracellular compartment consists of Type 1, 3, and 5 collagen fibers bundles embedded in intercellular substance. The periodontal ligament 22 collagen fibers are categorized according to their orientation and location along the tooth. The alveolar bone 21 is surrounded for the most part by the subepithelial connective tissue 28 of the gingiva 18, which in turn is covered by the various characteristic gingival epithelia. The attached gingiva 18 extends apically from the free gingiva 19 to eventually merge with the alveolar mucosa. The attached gingiva 18 is firmly bound to the underlying cementum 7 and alveolar bone 21 with collagen fibers of the connective tissue. The cementum 7 overlaying the tooth 1 root 12 is attached to the adjacent cortical surface of the alveolar bone 21 by the alveolar crest fibers 30, horizontal fibers 31 and oblique fibers 32 of the periodontal ligament 22. Transseptal fibers 33 extend interproximally over the alveolar bone 21 crest and are embedded in the cementum 7 of adjacent teeth; they form an interdental ligament. Transseptal fibers 33 keep all the teeth aligned, and can be considered as belonging to the gingival tissue because they do not have an osseous attachment. Periodontal vessels 26 surround the root and supply blood from the alveolar through channel 27.

The interface between a tooth 1 and the surrounding gingival tissue 19 is a dynamic structure. The gingival tissue forms a crevice surrounding the tooth 1, similar to a miniature, fluid-filled moat, wherein food debris, endogenous and exogenous cells, and chemicals float. The depth of this crevice, known as a sulcus 16, is in a constant state of flux due to microbial invasion and subsequent immune response. The gingival sulcus 16 is a space between the tooth 1 surface and a narrow, unattached cervical collar 20 of free gingiva 19. Located at the depth of the sulcus 16 is the epithelial attachment 29, consisting of approximately 1 mm of junctional epithelium and another 1 mm of gingival fiber attachment, comprising the 2 mm of biologic width naturally found in the oral cavity. The sulcus 16 is the area of separation between the surrounding epithelium and the surface of the encompassed tooth 1.

The free gingiva 19 surrounds the tooth 1 and creates a cuff or collar 20 of gingiva measured from the gingival sulcus 16 of the attached gingiva extending coronally about 1.5 mm. The gingival sulcus 16 is lined with the sulcular epithelium 29. The sulcular epithelium is that epithelium which exists on the sulcular side of the free gingival 19 margin. The oral epithelium 28 exists on the other side of the free gingival 19 margin. It extends from the free gingival 19 margin to the junctional epithelium (averaging 0.69 mm in depth). The junctional epithelium or epithelial attachment is a band of tissue at the apical portion of the gingival sulcus 16 that attaches the gingiva to the tooth. The junctional epithelium averages almost 1 mm wide. The inner surface of the free gingiva 19 next to the tooth forms the gingival wall of the sulcus. A healthy gingival sulcus 16 measures approximately 1-3 mm in depth.

Figure 2:
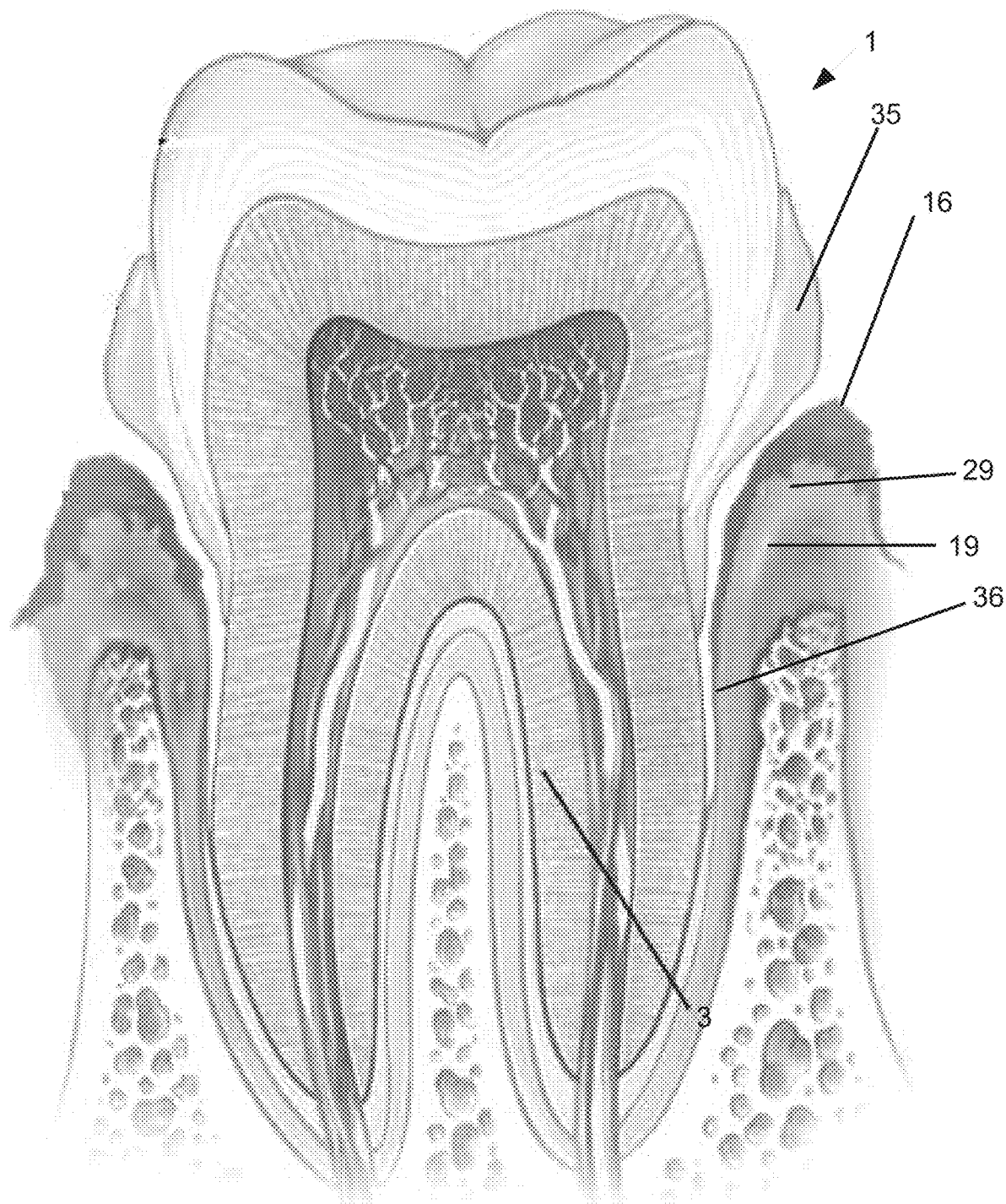
FIG. 2 illustrates a cross-section of a tooth in a periodontium with gum disease.

Gum disease falls into 4 stages, stage 1 gingivitis, stage 2 early periodontitis, stage 3 moderate periodontitis and stage 4, advanced periodontitis. FIG. 2 shows a cross section of a tooth 1 in a periodontium 17 afflicted by periodontitis. The inner surface of the free gingiva 19 next to the tooth 1 forming the gingival wall of the sulcus 16 is inflamed, swollen and eroding as it pulls away from the tooth, forming a sulcular pocket 36. In stage 1, this phenomenon is referred to as a gingival pocket. The epithelial attachment 29 does not migrate, it simply remains at the same attachment level found in pre-pathological health. The only anatomical landmark experiencing migration is the gingival margin in a coronal direction. In a gingival pocket, no destruction of the connective tissue fibers (gingival fibers) or alveolar bone occurs. Histologically, one would expect to find an inflammatory cell infiltrate. Biofilm 35, or plaque, has formed on the outer wall of the tooth 1 and is penetrating along the cementum 7 into the subgingival region. The biofilm 35 is made of colonies including bacteria that are suited to the periodontal eco-system. Pathogenic causing bacteria can appear in oral biofilms that are not disturbed on a regular basis by conventional oral hygiene procedures like brushing and flossing. As gum disease progresses, the disease-causing bacteria infect the periodontal pockets 36 around the teeth and become increasingly difficult to remove. Stage 1 gingivitis presents with inflammation of the gingiva, but without bone loss. This early sign of disease in the mouth is completely reversible when the etiology of the edematous reaction is eliminated and frequently occurs without dental surgical therapy. However, in certain situations, a limited dental periodontal surgery procedure is necessary to reduce the gingival pocket depths to a healthy 1-3 mm.

In the absence of routine oral care, most people develop gingivitis. In those who develop periodontal disease, pathogens such as bacteria in the biofilm 35 and enzymes from the body's immune response can progress to periodontitis, continuing to erode the tissues and form a periodontal pocket 36 ultimately destroying the alveolar bone 21 and the connective tissue of the gingiva 18 and loss of the tooth 1

Figure 3A:
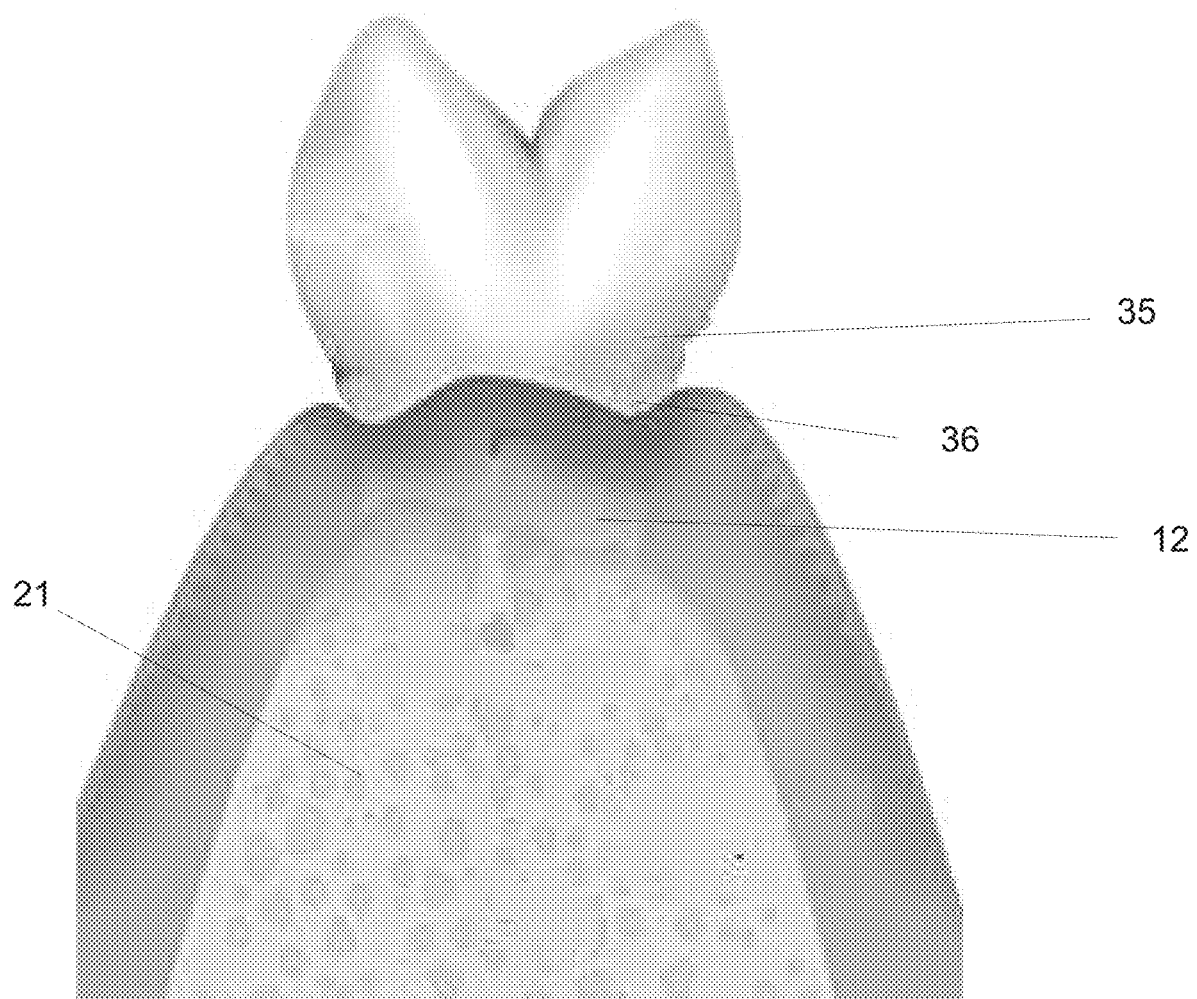
FIGS. 3A-3C depict a tooth and periodontium in progressive stages of periodontitis.
Figure 3B:
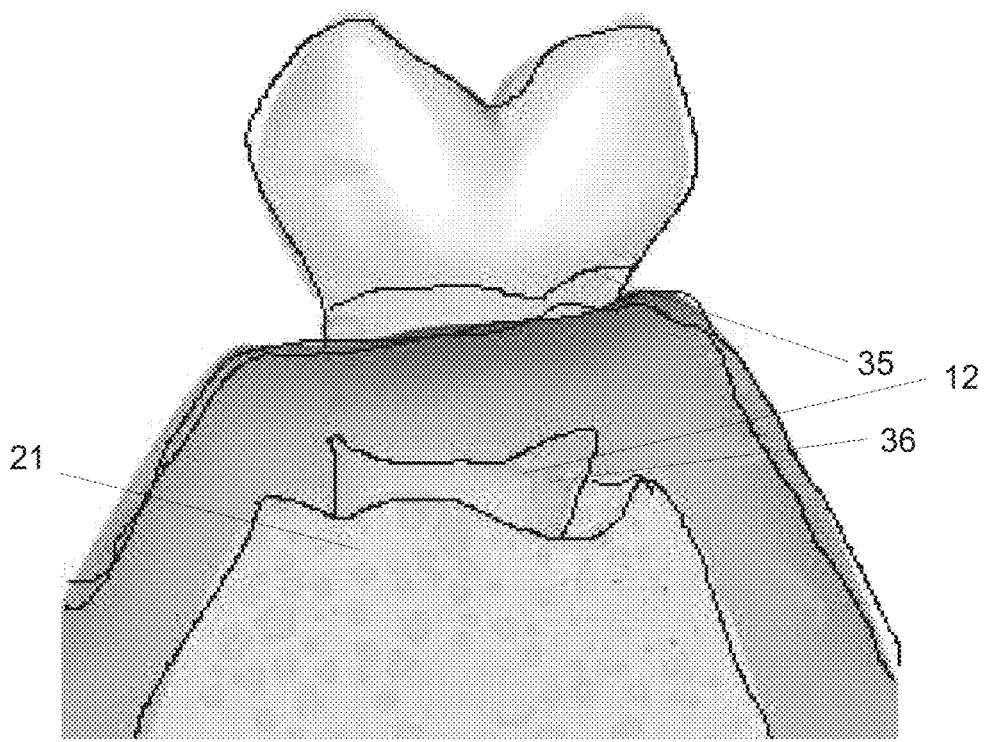
Figure 3C:
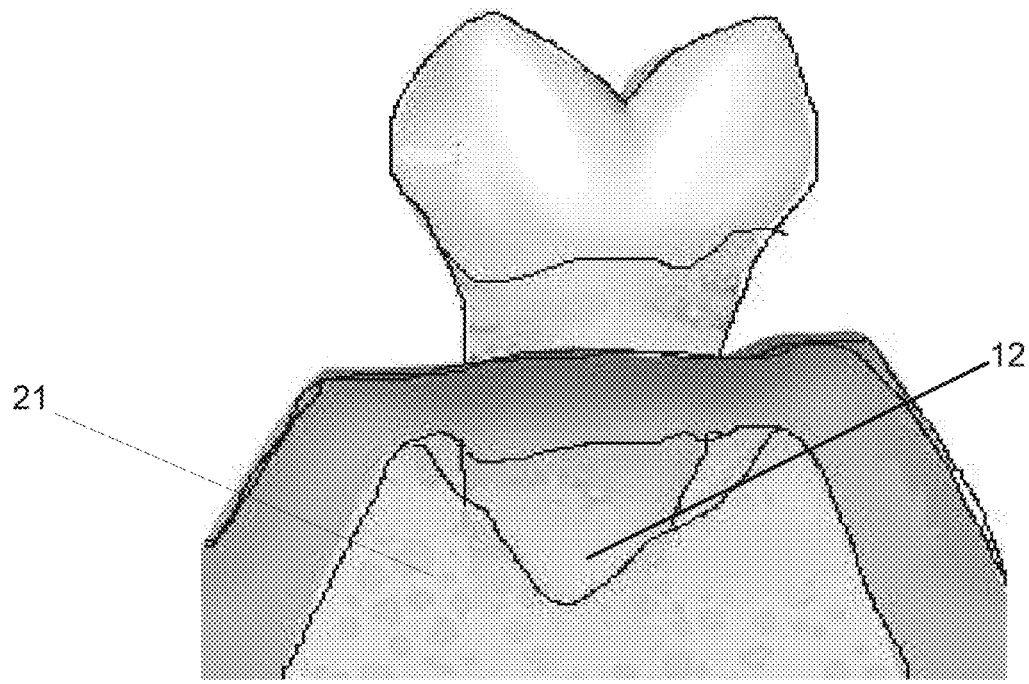

FIG. 3A-3C respectively show the 3 progressive stages of periodontitis. As shown in FIG. 3A, stage 2 early periodontitis results in inflammation of the gingiva and the surrounding tissues and early bone loss. FIG. 3B shows stage 3 moderate periodontitis, with inflammation of the gingiva and surrounding tissues, with the root 12 of the tooth becoming exposed and the biofilm 35 forming tartar 36 around the root 12, resulting in moderate bone 21 loss. At stage 4 advanced periodontitis, as shown in FIG. 3C the gingival inflammation is severe and several millimeters of the root are completely exposed. The biofilm tartar has penetrated into the root 12 and there is significant loss of the alveolar bone 21 and connective gingival tissue. The periodontal ligament 22 undergoes drastic changes with chronic periodontal disease that involves the deeper structures of the periodontium 17 with periodontitis. The fibers of the periodontal ligament 22 become disorganized, and their attachments to either the alveolar bone proper or cementum through Sharpey fibers are lost because of the resorption of these two hard dental tissue. Sharpey fibers are the ends of the principal fibers that are within either cementum or alveolar bone 21.

Conventional treatments for periodontitis depend on the severity of the disease. As noted above, a healthy periodontium will present with a sulcus measuring approximately 1-3 mm in depth. The precise millimeter measurement of sulcus depth is obtained using an instrument known as a periodontal probe. Clinically, the healthy gingival sulcus ranges in probing depth from about 1-3 mm and should not bleed when correctly probed. During clinical probing, a periodontal probe usually penetrates slightly into the junctional epithelium. A sulcus measuring greater than 3 mm usually indicates an unhealthy periodontium and is therefore best described with the use of the word "pocket."

As the original sulcular depth increases and the apical migration of the junctional epithelium has simultaneously occurred, the pocket is now lined by pocket epithelium (PE) instead of junctional epithelium (JE). To have a true periodontal pocket, a probing measurement of 4 mm or more must be clinically evidenced. In this state, much of the gingival fiber that initially attached the gingival tissue to the tooth have been destroyed. The depth of the periodontal pockets must be recorded in the patient record for proper monitoring of periodontal disease. A periodontal pocket can become an infected space and may result in an abscess formation with a papule on the gingival surface. Incision and drainage of the abscess may be necessary, as well as systemic antibiotics; placement of local antimicrobial delivery systems within the periodontal pocket to reduce localized infections may also be considered.

As part of the initial complete clinical dental comprehensive examination, periodontal probing depths along with all the other periodontal parameters are recorded for each tooth. Client assessment, treatment planning individualized for each tooth as well as the entire dentition addressing client needs, oral self-care instruction, preventive and non-surgical periodontal therapy, supportive treatment for health maintenance, and reevaluation are all critical components of thorough periodontal care.

Periodontal health and treatment can continue over the course of many years, and in some cases, over a lifetime of regular treatment and maintenance. Periodontal therapy typically falls into three phases:

Phase I Therapy: a nonsurgical phase, followed by an evaluation of the response to the nonsurgical phase;

Phase II Therapy, a surgical phase; and

Phase III a periodontal maintenance phase.

Phase I therapy, the nonsurgical preliminary phase of treatment, includes plaque control and patient education on oral care and diet, removal of calculus and root planning, correction of factors effecting restorative and prosthetics and influencing periodontal health, pulpal therapy if needed, and excavation of caries along with temporary or final tooth restoration. The nonsurgical phase can also include local and/or systemic antimicrobial therapy, occlusal therapy, minor orthodontic movement, and provisional splinting and prosthesis. The nonsurgical phase is followed up by an evaluation, in particular, checking pocket depth and gingival inflammation as described herein as well as rechecking biofilm, calculus and caries as part of comprehensive care.

If Phase I Therapy is determined to be ineffective in areas of the mouth dentition, treatment can progress to Phase II, the surgical phase. In order to create a more permanent, healthier environment around the teeth, periodontal surgery may be recommended in areas of the mouth that do not respond to non-surgical treatment. Soft tissue plastic surgery may be needed to improve cosmetics, or regenerative surgery, and may be necessary to rebuild and replace the lost bone support around the teeth. During periodontal surgery, the doctor has an opportunity to visibly ensure that all calculus (tartar) on the root surfaces has been thoroughly removed and more importantly that proper root planing is accomplished to provide the tooth root surface with a biologically clean surface. Dental implants may at this phase of treatment, be placed in edentulous sites if planned. Shallower pockets are easier to maintain both for the patients and the dental professionals who regularly and periodically clean their teeth and treat their gums.

Finally, the maintenance phase, Phase III Therapy, comprises periodic rechecking of the periodontium. This includes checking for plaque and calculus, gingival condition such as pockets and inflammation, occlusion, tooth mobility, and any other pathological changes. For many subjects, gum and periodontal disease should be addressed as a chronic condition, with Phase III Therapy lasting a lifetime.

As will be appreciated, optimal periodontal therapy with Phase I treatment avoids Phase II, and can be effective with only nonsurgical treatment at Phase I and with resolution of the infection and followed with maintenance at Phase III. It is best if nonsurgical treatment can fully address the causes of gingival and periodontal disease, fully stopping its progression. Mechanical debridement, for example such as scaling and root planning, is considered a nonsurgical treatment. Scaling and root planing is a careful cleaning of the root surfaces to remove biofilm—plaque and calculus (tartar)—from deep periodontal pockets and to smooth the tooth root to remove bacterial toxins. After scaling and root planing, while many patients do not require any further active treatment, the majority of patients will require ongoing Phase III maintenance therapy to sustain periodontal health. Conventionally, scaling and root planing is sometimes followed by adjunctive therapy such as local delivery antimicrobials, systemic antibiotics, and host modulation.

Phase II therapy involves surgical procedures when Phase I treatments are insufficient, for example when there is impaired access for scaling and root surface debridement. Conventionally, Phase II treatments are indicated when, for example, periodontal pockets are 5 mm or over, where root fissures or concavities are present, furcation defects are present, or infections persisting in periodontal pockets around implants or related to restorations. Periodontal surgery is performed to, among other things, gain access for thorough debridement and root scaling, reduce pocket depth and repair and improve the condition, function, and aesthetic appearance of the periodontium and surrounding tissues. This includes rebuilding lost structures, and sculpting the gingival morphology and margin for optimal biofilm control, restorative work and implants. If surgical intervention is required, it is optimal if it can be done with as little pain and inconvenience to the subject as possible. An optimal surgical treatment would be one that is streamlined or eased to the point that it is indistinguishable from a nonsurgical treatment in terms of patient discomfort and expense and is tooth site specific when possible.

Pocket therapy is a regular treatment for periodontitis and can involve surgical or nonsurgical techniques. As noted above, periodontitis destroys supporting tissue and bone in the periodontium, forming pockets that provide hospitable ecosystem for pathogenic bacteria. Deep pockets collect more bacteria, resulting in further bone and tissue loss, and ultimately, loss of teeth. During a periodontal pocket reduction procedure, a periodontist folds back the gum tissue and removes the disease-causing bacteria, for example via mechanical debridement, before securing the tissue into place. in some cases, irregular surfaces of the damaged bone are shaped to limit areas where disease-causing bacteria can hide. this allows the gum tissue to better reattach to healthy bone and the tooth surfaces.

A practical approach to nonsurgical periodontal therapy (Phase I therapy) includes the therapeutic advantages of scaling and root planing and merging it with periodontal debridement for enhanced root planing.

The American Dental Association's specialty organization, the American Academy of Periodontology (AAP) has treatment guidelines stating that periodontal health should be achieved in the least invasive and most cost-effective manner. This is often accomplished through non-surgical Phase I periodontal treatment, including root planing and scaling (a careful cleaning of the root surfaces to remove plague and calculus (tartar) from deep periodontal pockets and to smooth the tooth root to remove bacterial toxins), with adjunctive therapy such as local delivery of antimicrobials, systemic antibiotics as needed on a case by case basis, depending on the severity of the disease.

Enhanced scaling as described herein is a process by which dentists and hygienists remove bacterial plaque (Biofilms), calculus, stains, food debris and other accretions from the surfaces of the tooth. Root planing is a separate procedure that can be performed at the same time as the scaling, but is optimally performed at separate appointments when reevaluation of periodontal therapy healing is repeatedly checked at each remaining pocket site in the dentition from the initial scaling during multiple visits of Phase I periodontal therapy.

Enhanced root planing as described herein is a definitive treatment procedure designed to remove cementum or surface dentin that is rough, impregnated with calculus, or contaminated with toxins or microorganisms. In particular, enhanced root planing as described herein is the process by which residual embedded calculus and disease root cementum are removed from the tooth surface along with other surface contaminants to produce a smooth, hard and biologically clean surface. This helps allow a patient's oral tissues, namely, the periodontal (gum) tissues, and supporting bone to repair and regenerate on the tooth root surfaces of the dentition. Disclosed are embodiments for enhanced root planing with dental instruments including refined functional optimized working surfaces for controlled finishing by creating a functional cutting edge or working surface, one appropriate to both the instrument and its intended use.

For example, described herein are dental instruments including smooth and sharp cutting edges configured specifically for dental procedures to create as close as possible a root surface smoothness. Root surface smoothness should, if possible, be similar to the white enamel of a tooth, kitchen glass or other smooth surface to minimize bacterial growth and help prevent repopulations of microorganisms on the root. Root surfaces are tested for smoothness with special instruments by the clinician during and immediately after treatment.

For most patients of advanced periodontal disease, those having periodontal disease pocket depths of 5 mm to 10 mm or more, the favorable reduction in disease parameters occurs when root planing and scaling or enhanced root planing is performed repeatedly for each tooth for each of 4-6 visits over 4-6 months. Clinical research for disclosed embodiments herein indicates significant periodontal health improvements with recordings of bacterial scores, bleeding on pocket probing, probing pocket depths and probing attachments levels following 4-6 months after start of therapy. For some patients, additional time resulted in further improvements in the clinical periodontal parameters where pocket probing depths decreased from 8-9 mm down to 3-4 mm, with restoration of clinical health. Patients with severe periodontitis and the subsequent resultant bone loss heal mostly by repair with the gingival tissues, creating a new epithelial attachment to the roots of teeth and, to a lesser degree, by a long connective tissue attachment according to the periodontal research.

Early research such as published in the Journal of Periodontology 1984, by Beaumont R H, et al. shows that despite loss of a true periodontal attachment apparatus with alveolar bone loss for the tooth periodontal complex from ligature—soft diet induced bacterial plaque periodontitis in beagle dogs, there appears to be no appreciable difference in resistance to disease between a long junctional epithelial adhesion and a true connective tissue attachment. Light and fluorescent microscopic evaluation showed that neither group showed significant changes in location of the apical cells of the attachment epithelium following repair and healing during the post active treatment maintenance phase. Gingival health was maintained in both groups by daily brushing and by prophylaxis.

Many patients experience little or no discomfort when they have root planing and scaling done by an experienced periodontal clinician and require no anesthetics for pain or discomfort. Research indicates, however, that when pocket depths with clinical disease parameters persisting at some teeth despite the above described non-surgical approach to restore health, then periodontal surgery is indicated to visibly ensure that the root planing is thoroughly performed to allow for pocket probing depths to return to the 1-3 mm normal range and complete this root planing treatment task properly.

Periodontal debridement can be defined as the removal of all subgingival plaque and its by-products as evidenced by clinical signs of inflammation, clinically detectable plaque retentive factors (calculus, overhangs), and detectable calculus-embedded cementum, to finish the root surface during periodontal instrumentation while preserving tooth root structure where possible. This approach requires clinical judgement as to tissue response regarding any remaining presence of inflammation as well as re-evaluation for remaining biofilms and/or calculus and using tactile and visual skills. Reevaluation of healing following periodontal debridement is the key mechanism for ascertaining efficacy by evaluating the periodontal tissues for the elimination of inflammation, absence of bleeding upon probing, and levels of attachment and gingival recession. Long-term success then requires the cooperative maintenance care by both the patient and the clinician. The goals of periodontal therapy are to eliminate or suppress infectious microorganisms and other etiologic factors, and to establish an environment which promotes health of the periodontal tissues and precludes further loss of attachment. Disclosed are embodiments of a nonsurgical approach that supplies a predictable and conservative approach in treating shallow to moderate and deep pockets.

Reevaluation of the response to the above Phase I treatment is indicated after a suitable length of time as to resolution of inflammation and bleeding upon probing. If reevaluation following initial, nonsurgical therapy indicates that areas of the mouth have teeth with persistent inflammation and infection that is still not resolved and/or disease progression has occurred, a clinical decision must be made regarding the reason(s) for nonresponse and the need for further therapy including site specific periodontal surgery. Problems with self-care by the patient at home, inflammation or residual calculus and biofilms may require reinstruction, redebridement or in some rare occasions a different chemotherapeutic approach. A more aggressive therapy may be needed. Surgical and further non-surgical therapy may be needed on a site specific basis. Each individual's immune system may be capable of healing a periodontal lesion in the presence of different levels of microorganisms. Reevaluation of healing following periodontal debridement is the only mechanism for ascertaining efficacy by evaluating the periodontal tissues for elimination of inflammation, absence of bleeding, and level of attachment with changes in probing pocket depths. If the ultimate therapeutic endpoints have been achieved, then an acceptable level of calculus, biofilms and other root surface contaminants and altered or diseased cementum has been removed with a favorable response by the patient's immune response.

The past and current research literature evaluates most periodontal treatments including chemotherapeutic agents in human and animal clinical trials are with very limited research population trials (most with less than 100 patients, or animals) and longevity (most 6 months or less), with minimal significance of results to assess with good statistical conclusions the success for long term lifetime care. In contrast, embodiments described in the present disclosure are supported by testing and work with thousands of periodontally active disease tooth sites in thousands of patients, and is informed by the understanding that long-term success requires continued cooperative maintenance care by both the patient as a co-therapist. Accordingly, described are embodiments of chemotherapeutic and mechanical agents which can be employed by a clinician as well as a clinician and patient working together as co-therapists.

In periodontal diseases, microbial pathogens trigger inflammatory host responses which, along with direct irritation by bacterial products and byproducts, cause most of the destruction to the periodontium. The host must first recognize at some threshold level, and react to bacterial irritants for the disease to develop and progress. In most infections, the immune system localizes the invasion site and attempts to rapidly neutralize, destroy, or remove the foreign bacterial derived agents. The long-term presence of the bacteria plaque and its maturation with developing microbial colonization, causes a persistent and excessive host response that can varies in intensity depending upon host susceptibility. Research continues to identify susceptibility and who is "at risk" as well as identification of specific risk factors.

After the 4 to 6 visits spread over 4 to 6 months or more (as needed) of repeated scaling and root planing, reducing the number of active disease sites by this repeated effort at each remaining active disease pocket site or recession site and with gradual reductions in pocket probing depths noted at each visit initial periodontal therapy, the periodontal probing depths are recorded again and again. Site specific therapy is the goal: decisions made after no further favorable changes are noted after the usual 4-6 month period. However, site specific treatment planning may require additional time for some treated areas while others are ready for long term maintenance care, while still others need Phase II therapy or other forms of dental care. During and following completion of Phase I, Phase II Therapy and at future visits for Phase III Therapy, a complete detailed re-evaluation should be made using the following guide to assess sites responding to treatment for life time success. The clinician should include the following observations for each tooth with any recommendations for site specific therapy to follow.

Both observations and therapy should be carefully recorded. An evaluation of each tooth should include, among other parameters:
1. Nature of the healing of the gingival tissues: (edema, bleeding upon probing, suppuration, fibrosis.)
2. Gingival architecture: (enlarged, hyperplastic, thickened margins, clefts, craters).
3. Significant pocket depths and types of pockets: (4 mm. or more depth, gingival, periodontal or combined with infrabony defects). Pockets show clinical signs of active periodontal disease.
4. Furcation involvement: (incipient furcation less than 1 mm, more than 1-2 mm. depth furcation involvement, through-and-through furcation involvement with or without gingival soft tissue closure, trifurcation or bifurcation), Class I, II, III, IV. However, a more clinically relevant classification of furcation involvements should go beyond the horizontal component of bone loss and include a sub-classification of furcation involvements that measures the probable vertical depth from the roof of the furca apically. The subclasses are: A, B and C: "A" indicates a probe-able vertical depth of 1-3 mm, "B" 4-6 mm, and "C" 7 or more mm of probe-able depth from the roof of the furca apically. Furcations would thus be classified as IA, IB, 1C, IIA, IIB, IIC, and IIIA, IIIB, IIIC. Reference is: classification of the vertical component of furcation involvement. Tarnow D, et al. J Periodontol. 1984.
5. Pockets that are close to or beyond the mucogingival junction area: (following conventional surgical pocket elimination, and determine whether functional attached gingiva area is present or would remain after surgery—see #7 below).
6. Radiographic Evaluation: osseous defects (craters, one-two and three wall infrabony).
7. Functional attached gingival zones: Determine whether the forces produced by functional movement of the alveolar mucosa, freni, and muscle attachments are dissipated completely by the attached gingiva. Clinically, no bleeding, nor soreness upon periodontal probing, nor probing past mucogingival junctions. Monitoring with no further gingival recession developing.
8. Frena and muscle attachments related to clefts or interfering with surgical pocket depth elimination.
9. Vestibular depth: determine if it is adequate to permit a functional attached gingival zone after pocket elimination.
10. Changes in tooth mobility patterns.

The re-evaluation is merely a tentative guide and should be flexible and tooth specific, with possible future therapy changes being dictated by periodontal health changes. As further therapy progresses, constant evaluation should be a routine procedure. Complete evaluations are necessary at each recall visit for periodontal maintenance.

Furcation involvements are a common finding of the advanced periodontitis case.

The goals of the management of furcation findings whether there are vertical or horizontal components as discussed and defined above (see paragraph 4), should be creating an environment, preferably elimination of the furcation and at least adequate elimination of the furca, so that hygiene to control the repopulation of the microbial flora of the affected furcation can be maintained by both the clinician and patient, as well as enhance the capacity of the patient to maintain optimal oral hygiene. Disclosed are embodiments of combined chemotherapeutic/biomechanical intervention during Phase I, II and II that can enhance the success further for the lifetime retention of molars and bicuspid furcations using my methodology.

During and following completion of Phase I Therapy, Phase II (surgical) Therapy and at future visits for Phase III (maintenance therapy), a detailed re-evaluation should be made using the aforementioned and the following guides. Historically, the purpose of the re-evaluation is to carefully assay the response of gingival tissues to initial therapy—Phase I Therapy—including removal of calcareous deposits, oral supra and sub gingival biofilms (bacterial plaque control), oral physiotherapy, temporary stabilization, occlusal adjustment by selective grinding, orthodontics, endodontics, etc., to determine the subsequent treatment that may be indicated. As each of the clinician's observations are recorded, the treatment that is indicated should follow, such as periodontal osseous surgery, mucogingival surgery with augmentation techniques, tissue guided regeneration, autogenous and allographic bone grafting, etc. The re-evaluation as listed above in the aforementioned paragraphs, is merely a tentative guide and should be flexible and tooth specific, with possible future therapy changes being dictated by periodontal health changes. As further therapy progresses, constant evaluation should be a routine procedure. Complete periodontal evaluations are necessary at each Phase III recall visit for periodontal maintenance.

As noted above, periodontic therapy includes a number of treatments, including tooth extraction, occlusal correction, implant therapy and pocket therapy. Typically, the goals of periodontic therapy are, among others, to eliminate pain, stop and reduce pocket formation, reduce tooth abnormal mobility and arrest destruction of soft tissue and bone as well as restore lost tissue. In particular, the desired tissue response for localized and systemic treatment includes: restoring the surface continuity of the epithelium, reattachment of connective tissue between the alveolar bone 21 and the cementum 7, reattachment of the cementum 7 to the periodontal fibers, and restoring the balance between formation and resorption of the alveolar bone 21. The desired clinical results include elimination of pus formation, gingival bleeding and inflammation, elimination of periodontal pockets and infection, restoration of destroyed periodontal tissue, reduction of abnormal tooth mobility, arresting bone loss, and the restoration of the gingival contour to maintain health.

Local therapy includes biofilm removal as well has treatments to reduce the conditions for biofilms accumulation. Other local therapy treatment includes elimination of traumatized tissue to increase chances of bone regeneration and attachment. Local therapy also includes creating occlusal relations that are favorable to periodontal tissue, in particular, reducing tooth mobility and increasing the margin of safety plaque biofilm in the periodontium.

Systemic therapy is an adjunct to local therapy targeted to specific treatment issues, for example, controlling systemic complications from acute infections, chemotherapy to prevent harmful effects of post treatment bacteremia, supportive nutritional therapy, and control of systemic diseases that can aggravate periodontal treatment or may require special precautions. Conventional systemic therapy includes systemic antibiotics to eliminate bacteria that invade gingival tissue and may reinvade and repopulate the pocket. Other systemic treatments have been reported include NSAIDs such as ibuprofen and flurbiprofen to slow down development of gingivitis and loss of alveolar bone.

In one or more embodiments, described is dental treatment method comprising: providing a gel solution including a peroxide gel, for example a 10% carbamide peroxide, for administration to a treatment area of a subject in conjunction with a dental care treatment; and providing a viscous antibacterial agent including a clinically effective amount of tetracycline to the treatment area of a subject during the dental treatment. In embodiments, the peroxide gel solution chemically debrides and anesthetizes the treatment area. In an embodiment, the viscous antibacterial agent consists essentially of tetracycline.

In an embodiment, disclosed is a method for treating periodontal disease comprising: administering a gel solution including a peroxide to a periodontal pocket of a subject in conjunction with a mechanical debridement treatment, wherein the peroxide gel solution chemically debrides and anesthetizes the treatment area of the periodontal pocket; and administering a viscous antibacterial agent including a clinically effective amount of a tetracycline to the periodontal pocket of a subject during the mechanical debridement treatment.

A wide range of peroxide gels can be used. For example, gels can include, peroxide compounds, hydrogen peroxide, carbamide peroxide, peroxide containing materials, or any other agent that will undergo debriding oxygenation. The peroxide agents are provided in a gel or viscous state. Exemplary gel solutions include hydrogen peroxide gels, for example a gel with hydrogen peroxide 1.7% (w/w) (e.g., Periogel®), carbamide peroxide (hydrogen peroxide-urea) gels, which break down into hydrogen peroxide and urea, for example, Gly-Oxide®, which contains 10% carbamide peroxide and yields approximately 3.5 percent hydrogen peroxide when it breaks down. The gel concentration of peroxide can range from as little as 1.5% to as much as 44%.

In an embodiment, disclosed is a method for treating periodontal disease comprising: administering a gel solution including at least 10% carbamide peroxide to a periodontal pocket of a subject in conjunction with a mechanical debridement treatment, wherein the peroxide gel solution chemically debrides and anesthetizes the treatment area of the periodontal pocket; and administering an antibacterial agent consisting essentially of tetracycline to be administered to the periodontal pocket of a subject during the mechanical debridement treatment. Various antimicrobial gels or pastes or antibiotic gels or pastes can be administered together or separately.

In an embodiment, described herein is the use of sharpening tools to provide optimized functional working surfaces for dental instruments, for example optimized blades or cutting edges. These optimized dental instruments and working surfaces are influential in controlling or limiting bacterial growth rates and the potential for selective bacterial flora attachments to roots by controlled surface roughness along with the microbiological rates of other organisms such as virus fungi amoebas and other parasites varying surface roughness, and morphology on surface root substrates. This can enhance the effectiveness of antimicrobials and antibiotics as well as surgical regenerative and surgical epithelial and connective tissue repair and root reattachment procedures during Phase I and Phase II and Phase III treatments. Therefore, indirectly or directly, when the sharpening tool is used to refine dental instruments to optimize working surfaces, the enhanced root planing and scaling with such instruments during Phase I, Phase II, and Phase III is antimicrobial and helps prevent the repopulation of certain bacterial types in favor of other types.

In an embodiment, the tetracycline can be powdered tetracycline, which can be administered directly into the periodontal pocket before and/or during the mechanical debridement, where it obtains a viscous, paste-like consistency. In an embodiment, a medicament comprising the solution and the antibacterial agent can be administered in conjunction with the treatment. In an embodiment, the treatment can comprise nonsurgically treating advanced periodontitis such as in furcation sites such as molars and some bicuspids. For instance, diseased bicuspids can have deep vertical pockets in molars and some bicuspids where the pockets follow a convoluting course into the furca with horizontal and vertical pathways. Trays and other such delivery mechanisms do cannot reach these pockets nor adapt and fit under the clinical tooth enamel crown.

In an embodiment, the treatment can be administered to a subject at a pocket depth of 5 or more millimeters during the non-surgical mechanical debridement periodontal disease treatment. For example, the treatment can be applied at a periodontal pocket depth of at least 7 millimeters or even at least 10 millimeters. As will be appreciated, in assessing measurements, the length of the root surface and the individual anatomy of the roots and surface topography that are found on molars, bicuspids, canines and incisors can vary. As such, the extent of the periodontal attachment loss, whether hard or soft tissue, can be a determining factor in periodontal probing of pocket depths. Teeth such as molars and some bicuspids can also have furcation involvements between their multiple roots and these furcations can be further defined with loss of periodontal bone attachment and soft tissue attachments to their root surfaces with periodontal probing.

In an embodiment, the 10% carbamide peroxide solution as anesthetic is applied in an amount effective amount to forestall the need for injected anesthetics such as, for example, lidocaine (xylocaine). This allows for the treating periodontist to apply the treatment at pocket depths ranging from more than 3 mm to at least 5 mm without the need for other anesthetics, including up to at least 7-10 mm as described above. Conventionally periodontists would need to introduce a topical or injection of known anesthetics such as lidocaine or Novocain or stronger anesthetics for such aggressive mechanical debridement. Indeed, fear prevents many patients from obtaining dental care, whether it is fear of dental treatment, local anesthesia, or past dental experiences. Also, local anesthetics can cause stinging and burning upon injection, which may adversely affect fearful patients. Dental hygienists and dentists have the unique responsibility and opportunity to alleviate pain. Avoiding the use of local injected anesthetics altogether during non-surgical Phase I therapy by using 10% carbamide peroxide or topical anesthetics, refined dental instruments with optimized working surfaces such as sharp smooth cutting edges with no wire edges on dental curettes and scalers, and a good choice of clinical instrumentation and clinical skills go a long way in having a cooperative, non-apprehensive patient, who will return for continued dental care with a level of patient comfort avoiding the use of analgesics post treatment. The overwhelming majority of patients do not need injected local dental anesthetics during scaling and root planing and enhanced root planing procedures except during Phase II surgical care.

Root desensitization products also should be used first where root instrumentation is a concern at specific tooth sites that could result in discomfort and thus avoid the use of local anesthetics for pain management.

It is expected embodiments of the technology and methods described herein will justify changes in standards of care.

As will be appreciated, properly sharpening the working edges of dental tools, for example curettes and other scalers, reduces even further the need for powerful anesthetics. Treatment, when administered in conjunction with properly sharpened dental tools with functional optimized working surfaces, can smooth tooth root surface to 1-5 microns—down to 1 micron. Root conditioning to this degree of smoothness makes the root inhospitable to bacteria and pathogens as the bacteria cannot attach to the root. Thus, the repeated application of the chemical debridement properties of the gel was able to non-surgically treat many pocket sites at 5 mm and even greater, to over 10 mm, without surgery. Smoothing the roots to as close as 1 micron root results in surface finishing that is as smooth as possible. As will be appreciated, removing various bacterial and non-bacterial substances supragingivally and in the exposed pocket/sulcus helps reduce the future bacterial recolonization of smooth root surfaces. The unique chemical approach described in embodiments herein achieve a chemical curettage and root conditioning that improves the removal of bacterial and non-bacterial substances. Antibacterial and antimicrobial approaches together with the chemical curettage and use of optimally sharpened tools achieves the most successful treatment and future preventive management of the periodontal and dental caries/decay prevention. In various embodiments, described are periodontal treatments that includes a battery of professionally and patient-administered antimicrobial agents, mechanically intraorally, to provide effective, practical, safe and affordable means of controlling supra and subgingival colonization of periodontal and caries pathogens for the various types of diseases.

Embodiments as described herein can be employed to establish professional guidelines for optimal periodontal care requiring that root surfaces scaled and root planed should be made as smooth and biologically clean as possible to minimize the bacterial repopulation of root surfaces that leads to maturation of bacterial plaque which is responsible for Dental Caries and Periodontal Diseases and therefore, can help prevent a higher Periodontal and Dental Caries Disease Index in the population.

Numerous research articles published in the dental literature have determined the importance of using properly sharpened and finished curettes during the biomechanical root preparation in periodontal therapy. For example, a recent publication by Rossi and Smukler in The Journal of Periodontology points out the importance of using curettes sharpened and finished with finer grit stones and abrasives, as they produced smoother and finer root surfaces than those sharpened with rough or coarse grit stones or abrasives. The highest grit number (the greatest number of particles per square inch) produced the smoothest and sharpest cutting edges and these abrasives were the aluminum oxide and Arkansas stones (prior to the availability of optimized sharpening and shaping tools as described herein). They concluded that the smoothness of the planed root of the tooth is related to the type of sharpening stone or abrasive used during the sharpening or shaping process. As will be appreciated, the present disclosure includes optimized sharpening technology that is sharpens and shapes 5-6 times finer than the aluminum oxide and Arkansas stones available for that study.

Quirynen and Bollen reported on the influence of surface roughness and surface-free energy and subgingival plaque formation in humans. Journal of Clinical Periodontology (January, 1995). These authors reported on the iatrogenic effects of biomechanical root preparation during periodontal therapy from instruments acquired brand new from dental manufacturers and their influence on promoting bacterial plaque formation from severe metallic deformities and wire edges, extending along the cutting edge itself. Rough surfaces will promote plaque maturation, and high-energy surfaces are known to collect more plaque, to bind the plaque more strongly and to select specific bacteria. The current unifying world document on proper periodontal treatment modalities (The Annals of Periodontology: Proceeding of the World Workshops in Periodontics, November 1996) endorses and quotes the work and ideas of this extensive review article of Quirynen and Bollen in the importance of creating smooth root surfaces as an objective of proper biomechanical periodontal therapy.

Although both variables interact with each other, the influence of surface roughness overrules that of surface-free energy. For the subgingival environment, with more facilities for microorganisms to survive, the importance of surface characteristics diminishes. However, the influence of surface roughness and surface-free energy on supragingival plaque justifies the demand for smooth surfaces with a low surface-free energy to minimize plaque formation, thereby reducing the occurrence of dental caries and dental periodontitis in the world population. Therefore, in embodiments, tool shaping and sharpening can be performed in conjunction with each treatment using optimized sharpening tool technology described in U.S. Pat. Nos. 6,074,293, 6,361,408, 6,949,018, U.S. patent application Ser. No. 15/241,252, and International Patent Application PCT/US2015/041998, the entirety of each of which is incorporated by reference hereby, (e.g., Honing Channel™ Sharpening Systems). The design and engineering aspects of this technology helps to meet the clinical treatment needs defined by current dental research which ultimately benefit the patient.

Accordingly, in at least one of the various embodiments, the dental treatments include sharpening a dental instrument working surface with a sharpening tool configured to produce a cutting edge that optimizes the working surface of the blade such that the dental treatment is executed with the optimized blade. For example, during mechanical debridement such as enhanced root planing, a care professional can use sharpening tool with abrasives that sharpen dental instruments that will in turn make the roots of teeth very smooth to minimize biofilms repopulations on root surfaces, together with using antimicrobials and antibiotics described herein, for example topically applied carbamide peroxide gel and tetracycline during treatment. In an embodiment, a patient (or patient caregiver) can also regularly use antimicrobials, for example 10% carbamide peroxide and even topical fluorides, on the roots to minimize dental decay risks. For example, a patient or patient caregiver can be instructed to floss with a gel solution comprising at least 10% carbamide peroxide as well as use a topical fluoride (e.g. Prevident™) during the active period of the disease and even after during long term maintenance care.

In at least one of the various embodiments, in conjunction with each treatment, dental tools are sharpened to fine cutting edges such that that the smoothness and sharpness of the functional working surface of the tool is replicated on the root surfaces. The optimized dental tool can then be used together with the pharmaceutical methodology described herein to achieve greater success and minimize the periodontal disease index and the caries disease index.

In at least one of the various embodiments, a mechanical treatment comprises smoothing the roots using enhanced root planing to as close as a 1-5 micron root surface. The surface finishing is as smooth as possible and removes various bacterial and nonbacterial substances, which helps treat disease supragingivally and in the exposed pocket/sulcus and also helps prevent disease by reducing the future bacterial recolonization of root surfaces. As described herein, in embodiments dental tools can be sharpened to obtain optimized to cutting edges at 1 to 5 microns, which in turn can create a root surface finish to 1 to 5 microns as well. Sharpening tools as described herein can also produce optimized cutting edges that have no wire edges.

Since 1995, advances in research, development, and optimized sharpening tool technology as described in U.S. Pat. Nos. 6,074,293, 6,361,408, 6,949,018, U.S. patent application Ser. No. 15/241,252 and International Patent Application PCT/US2015/041998, have resulted in engineered channels to properly reshape or resharpen either European or American curettes and sickle scalers. For example, The Honing Channel™ Sharpening Systems for curettes and sickle scalers include high strength, custom designed aluminum oxide sharpening and shaping stones. As sizes vary amongst instrument manufacturers, these ceramic stones have built-in tolerances in the channels, to accommodate most curettes and scalers used by the vast majority of dental professionals worldwide. For example, based upon the World Workshops in Periodontal Therapy, the White Honing Channel™ Sharpening Stone was created having the highest grit (the greatest number of particles per square inch) and the greatest density; one of its main purposes is to give the sharpest and finest cutting edge possible, a prerequisite for successful quality periodontal therapy. In an embodiment, the White Honing Channel™ Sharpening Stone includes a 0.472"×0.984"×3.93" stone that is 3.5 oz.

In another embodiment, the Chocolate Honing Channel™ Sharpening Stone includes 0.495"×1.03"×3.93" stone that is 3.3 oz. In another embodiment, the sharpening tool can include 3.93" sharpening sticks of 0.2 oz.

In various embodiments, the optimized sharpening tool technology described herein improves the quality and delivery of Dental treatment and healthcare by the clinician and ultimately for the benefit of the patient by properly preparing dental instruments for clinical use based upon current accepted professional standards and advanced professional standards of care proposed herein. The optimized sharpening tools consistently provide the smoothest and sharpest cutting edge on any metal alloy, ceramic, or plastic of any manufactured instrument by anyone who uses it. As explained herein, dental research studies indicate that the smoothness of the root surface in periodontal treatment is directly determined by the smoothness and finish of the cutting edge of the dental instrument and those cutting edges finished with those sharpening stones having the highest grit and finest abrasive levels (highest grit) produced the smooth and finest cutting edges which were replicated on the tooth root surface during scaling and root planning treatment. Despite this, as of the filing of the present application, new dental curettes and scalers are not properly finished as they come from the manufacturer, and require proper finishing first to remove the wire edges found on the cutting edges of these new instruments before they are used in treatment. In addition, as few as 15 to 30 strokes on the root of a tooth can appreciably dull and damage a cutting edge and therefore, the instrument's cutting edge constantly needs correction with reshaping and re-sharpening during the patient's visit. The use of the optimized tool technology, for example the Honing Channel™ sharpening and shaping channels will quickly reshape and resharpen only the cutting edges of curettes and sickle scalers in as little as 1 to 3 strokes in the channel saving, chair time. Optimized tool technology simplifies the entire sharpening procedure and permits licensed medical/dental clinicians to sharpen chairside during patient care delivery and also now permits non-licensed technicians in the lab or sterilization/technician area to sharpen and have them ready for use in treatment with all types of curettes and scalers with less than one hour of training. No matter who uses the product on the medical/dental team, the same correct consistent sharp highly refined cutting edge will be created true to its original geometric design for consistent quality care, unlike with earlier ad conventional 'flat stone' sharpening technology used up to today.

Previously, the manufacturing of scalers and curettes has been performed by hand, using flat or rounded abrasives, which require the utmost skill of the technician or clinician to find the precise angle between the instrument and the shaping and sharpening device. Great difficulty is encountered in finding this precise angle of the dental-medical instrument and maintaining this angle along the entire length of the cutting edge during the sharpening and shaping process. Further, one of the problems in finishing these complex surfaces, especially curvilinear surfaces (such as the cutting edges found on the cutting blades of curettes and scalers) is the need to draw the article across an abrasive surface while continuously changing the angle to accommodate the geometric shape thereof. The finishing of complex surfaces usually requires skilled hands, experienced craftspeople, or complex robotic manufacturing machinery. Even experts find it difficult to follow many complex surface shapes, due to the demanding control required.

In the manufacturing industry, establishing conditions for a finishing process to obtain a specified surface topography also is not problem-free, since many interacting factors are involved. Under ideal circumstances, the factors to be considered involve the operational setting of the machine (e.g., the geometric characteristics of the abrasive tool, the work speed, the tool feed rate and the type of cutting fluid used). Even under ideal conditions, it has been only possible to calculate the theoretical roughness developed in a machining operation for the simplest process, i.e., single-point tool cutting. The fact that it is not possible to fully specify the characteristic and surface scale and topography of a surface remains a serious problem for production/design engineers.

One aspect of the embodiments of the sharpening tool concerns the finishing of surfaces on tools and instruments. For example, dental, veterinary and medical instruments may have sophisticated shapes, which can only be obtained with an exacting and complex finishing procedure. Accordingly, in at least one of the various embodiments, described is a sharpening tool that accurately provides an exactly shaped cutting edge to a dental tool, for example a dental curette, suitable for proper biomechanical root surface preparation in periodontal therapy. The apparatus not only provides an exact shape for the curette cutting edge, but it does so with precision every time. With this optimized sharpening apparatus, the dentist or technician performing the finishing, need not be as careful as drawing the instrument across the abrasive surface. The optimized sharpening apparatus has one or more specifically shaped abrasive surfaces to guide and shape the instrument surface. These abrasive surfaces of the channel of optimized sharpening tool creates an exact shape for the cutting edge of the curette. The shape of the channel provides the fineness and delicacy of the original design of the curette that is replicated on the root surface. The fineness of the cutting edge was established at 1 to 5 microns, creating a root surface finish finer than could ever be achieved previously.

Advances in research, development and technology in the field of ceramics have resulted in custom-designed aluminum oxide sharpening and shaping stones.

The concept of sharpening and shaping channels can now permit, with this application of optimized sharpening tools, licensed dental personnel and most non-licensed dental personnel to learn to sharpen the curette in less than one hour of training. There is a significant savings in professional time and money as hygienists and dentists can now quickly and accurately sharpen their scalers and curettes or delegate this responsibility to a technician or assistant and have the instrument sharpened and finished properly and ready for use. Studies indicate that most graduate dentists and hygienists cannot consistently sharpen adequately their required dental instruments due to inadequate university professional training during their professional careers and this problem carries on afterwards during their professional careers. An important aspect of professional practice is proper instrument preparation prior to use, which has been seriously overlooked up to now for each patient during dental treatment and clearly is a world-wide healthcare problem. This product can help once again motivate professionals to perform sharpening for each patient and meet this needed responsibility in service to their patients. These engineered sharpening channel stones have not been available with accurate channel designs previously. The applications of these patents cross into the medical and veterinary fields and across other manufacturing lines.

The optimized sharpening tool in embodiments as described herein, consistently keeps instruments true to their original geometric designs, prolongs the life of instruments by minimizing wear and abrasion unlike other sharpening stones used in dentistry (the Arkansas stone), closely restores the root to its original level of surface smoothness. Moreover, there is no oil lubrication necessary, and instruments can be sharpened correctly for each patient. The dental practice team can now sharpen consistently create and restore the same cutting edge no matter who uses it, unlike other techniques (e.g., flat stones trying to place the correct angle or shape).

Accordingly, in at least one embodiment, the method includes providing a finishing tool for sharpening a dental instrument. Exemplary sharpening tools are described below and in U.S. Pat. Nos. 6,074,293, 6,361,408, 6,949,018, U.S. patent application Ser. No. 15/241,252 and International Patent Application PCT/US2015/041998, the entirety of each of which is incorporated by reference hereby.

For example, in at least one of the various embodiments, the method can include using finishing tool for surface finishing complex and simple surface shapes by abrasion of select zones of the surface, leaving contiguous zones unfinished. The apparatus can simple in construction and required little in training for operation. The apparatus can include an abrasive surface, which in cross-sectioned profile is negative image of the surface zone to be abraded of finished, and a relief surface corresponding to the zone or zone to remain unfinished.

In an embodiment, the apparatus for finishing a zone on the surface of a dental instrument, where the said surface comprising a plurality of adjacent and contiguous zones, which comprises; means for supporting a rigid abrasive surface; an inflexible, abrasive surface supported on the means for supporting said abrasive surface having (i) a cross-sectional profile which is a negative image of a profile of the zone to be finished; and (ii) a relief corresponding to the zone or zones to remain unfinished.

The abrasive surface can further comprise a relief connecting the pair of sharpening areas and being positioned below the pair of sharpening areas, the relief corresponding to the zone or zones to remain unfinished. A finishing area can be a linear surface or curvilinear surface. The apparatus can accurately provide an exactly shaped cutting edge to a bladed instrument.

The apparatus not only provides an exact shape for the bladed instrument's cutting edge with precision every time. In certain embodiments, the finishing apparatus is configured such that drawing the instrument, a dental curet for example, across an abrasive surface of the apparatus eased. Although the instrument itself is generally held at certain angles with respect to the abrasive surface, even this is not critical. The apparatus can one or more specifically shaped abrasive surfaces to guide and finish the instrument surface. These abrasive surfaces create an exact shape for the cutting edge of the curet. The shape provides the fineness and delicacy of its original design. Therefore, the abrasive surface component of the apparatus creates not only an exact shape of the desired cutting edge of a curet, but a cutting edge with the proper edge fineness and delicacy required in dentistry based on current research. A tool may be configured to sharpen multiple different bladed instruments or working surfaces by configuring a single finishing apparatus and finishing process with surface topography or surface geometry, cross-sectional geometry, and surface finishing for shaping, sharpening, and surface roughness control for a plurality of bladed instruments (e.g., one area for a dental curette, one area for a scaler, one area for surgical scissors, etc.).

In an embodiment, a sharpening and shaping device for dental and surgical instruments can comprise a block of hardened, abrasives material designed to abrade, cut or otherwise shape metal surfaces of said instruments, said block having a generally flat top surface containing at least one sharpening and shaping groove disposed therein, said at least one groove receiving a distal end of said instrument for the purpose of sharpening and shaping said distal end when said instrument is drawn through said groove, said at least one groove having an active cutting surface for shaping said distal end, and a relief surface for guiding said distal end in a non-cutting mode.

In an embodiment, the finishing device for the instruments' surfaces can comprise a block including abrasive materials designed to abrade, cut or otherwise finish surfaces of dental instruments, said block having a single block structure containing a finishing cavity, disposed therein, said cavity comprising at least a portion of a negative image surface of a portion of the instrument to be finished, said cavity further comprising at least one groove formed inside said cavity, for receiving a distal end of said tool or instrument for the purpose of finishing said distal end when said tool is moved relative to said at least one groove, said at least one groove having an active, cutting surface for finishing said distal end.

In an embodiment an apparatus for finishing a zone on the surface of an instrument can comprise a support for a rigid abrasive surface; one or more channels supported on the support, each of the channels having a cross-sectional profile including at least one finishing area to finish an operative zone of the article that optimizes a clearance portion of the article, wherein the finishing areas includes a contacting area and a non-contacting area, and wherein an angle of each finishing area of the cross-sectional profile is substantively the same as an optimal clearance angle of the article, wherein the apparatus is configured to position the operable zone of the article along the angle of the finishing area during sharpening. In certain embodiments, the one or more channels can each include a pair of the finishing areas. In certain embodiments, the clearance angle $\beta$ of the article is calculated as $\beta=90°-\gamma-\alpha$, where $\alpha$ is a rake angle and $\gamma$ is a blade angle. Exemplary sharpening tools are described in U.S. patent application Ser. No. 15/241,252 and International Patent Application PCT/US2015/041998, the entirety of which is incorporated by reference hereby.

Research studies in the Journal of Periodontology in 1994 and 1996 by Leknes, Lie, Wikesjo, Boe, and Selvig demonstrate that the character of subgingival root instrumentation by using different abrasives and creating different surface root roughness levels, altered the bacterial recolonization. These studies demonstrate that by altering the subgingival instrumentation roughness, one can significantly influence the subgingival microbial colonization. By these researches, altering the tooth instrumentation roughness they also found that the character of subgingival root instrumentations significantly affected gingival inflammatory reactions, most likely by influencing subgingival plaque. This is contributing evidence why embodiments as described herein works, by using a mechanical high level of root smoothness and a chemical approach, the clinician in the office, mechanical treatments (floss, brushing, stimudents) together with chemical treatments (e.g. peroxide gel, peroxide gel together with fluoride paste) by the patient at home.

The unique chemical approach as described herein alone or together with the optimized dental tools for mechanical treatment helps achieve the same beneficial treatment effect with a chemical curettage and root conditioning, which improves the same removal of bacterial and non-bacterial substances with antibacterial and antimicrobial approaches to achieve the most successful treatment and future preventive management of the periodontal and dental caries/decay prevention. The present approach includes and recommends a periodontal treatment that includes a battery of professionally and patient-administered antimicrobial agents, applied mechanically intraorally, to provide effective, practical, safe and affordable means of controlling supra and subgingival colonization of periodontal and caries pathogens for the various types of diseases.

In an embodiment, the method comprises administering a first application of the antibacterial treatment prior to applying a first administration of the solution. In an embodiment, the method comprises administering a first application of the solution prior to administering the antibacterial treatment. In another embodiment, the solution and the antibacterial treatment can be administered at the same time. For example, the treatment can be administered via a medicament comprising both the solution and the antibacterial treatment in a single delivery mechanism, for example a stable viscous gel solution that can be applied to the treatment area.

In an embodiment, the method comprises repeating the treatment a plurality of times during the active phase of the disease. For example, as noted above, a nonsurgical phase treatment is followed up by an evaluation, in particular, checking pocket depth and gingival inflammation as well as rechecking biofilm, calculus and caries. Accordingly, in an embodiment the treatment can comprise administering a follow up treatment comprising: applying or delivering the solution including the peroxide to a periodontal pocket of a subject; and applying or delivering the viscous antibacterial agent including the clinically effective amount of tetracycline to the periodontal pocket of a subject during the follow up. The treatment can be continued at some or all of each follow up visit during the active phase of the disease. In an embodiment, the treatment can be continued one or more times through the maintenance phase of the treatment as well.

In an embodiment, the method comprises instructing the subject to floss with the gel solution including 10% carbamide peroxide at least once daily for the active phase of the periodontal disease. In an embodiment, the method can also comprise instructing the subject to gumbrush with the gel solution including 10% carbamide peroxide at least once daily for the active phase of the periodontal disease. In an embodiment, the method can comprise instructing the subject to continue regularly flossing with the gel solution including 10% carbamide peroxide at least once daily during a maintenance phase of the periodontal disease. For example, the subject can be instructed to floss daily and/or as a part of the subject's regular (e.g. daily) dental care routine. As noted herein, the maintenance phase can continue throughout a subject's lifetime. Maintenance can include instructions to include site specific application of the peroxide gel when site specific analysis indicates where periodontal disease is known to form to support ongoing maintenance care.

In an embodiment, described is a dental treatment method comprising: providing a solution including a peroxide gel solution for administration to a treatment area of a subject in conjunction with a dental care treatment, wherein the peroxide gel solution chemically debrides and anesthetizes the treatment area; and providing a viscous antibacterial agent comprising a clinically effective amount of a tetracycline to the periodontal pocket or wound site of a subject during the dental care treatment. The dental care treatment can comprise, for example, treating a dental root for a bone graft, treating or preventing peri-implant mucositis and peri-implantitis (e.g. from a titanium implant), treating a dental surgery tissue with autograft or allograft transplants, and other materials in the surgical methodology for treating the root of the subject (e.g.: root plaining or root conditioning, or a root canal treatment. The use of the tetracycline can also be used with surgical membranes placed with hard and soft tissue grafts associated with edentulous ridges as well as dental implants or natural tooth roots. These chemotherapeutic agents not only act as a tooth root conditioner, they assist in the surgical debridement and wound conditioning of the adjacent biologic soft and hard tissues, whether supporting a natural tooth, a dental implant, edentulous ridge, various surgical membranes or extraction site minimizing post-operative pain, swelling, and other sequelae such as infections.

Doctors who have never experienced implant failures or complications likely either have not performed enough of them or their patients are seeking the care of another doctor for treatment of problems they experience. Although reported to achieve long term success, dental implants are not immune from complications associated with improper treatment planning, surgical and prosthetic execution, material failure, and maintenance. Those complications that are biologic in nature include peri-implant mucositis and peri-implantitis, and are inflammatory conditions in the soft and hard tissues around dental implants.

In at least one of the various embodiments the method can further comprise: sharpening or finishing a dental instrument working surface with a finishing tool; and performing optimized surface finishing for dental implants with the sharpened or finished dental instruments. The finishing tool is configured to produce an optimized working surface of the blade or functional edge such that the implant surface finishing treatment is executed with the optimized working surface. The finishing tool can be configured to produce an optimized working surface for an instrument including, for example, no wire edges, no deformations, and/or a working surface finished to the tolerances of the implant.

In an embodiment, provided is a tool with an optimized working surface that can produce a controlled finished surface for an implant in vivo. For example, a finishing tool can be configured to retap or reshape an the body of an implant. The tool can include, for example, a reverse thread that finishes, resurfaces, or recuts the thread of the implant, depending on need of the patient. For example, in certain embodiments, a screw sharpening or shaping apparatus can include blocks or housings, each of which can contain one or more grooves with abrasive areas, such as described in International Patent Application PCT/US2015/041998 and U.S. patent application Ser. No. 15/241,252, the entirety of each of which is incorporated by reference hereby. The grooves form a channel when the housings are closed together. To sharpen or shape the screw, the housings can be positioned or closed over screw such that it is located in the channel formed by the grooves in each of the housings. In an embodiment, the grooves can have the same thread pattern corresponding to the thread on the implant screw. Therefore, when the screw is positioned in the groove channel, rotating the screw along the threads will impart with precision a particular shape to the thread of the screw. In an embodiment, the channel can be configured to impart different shapes or controlled surfaces to the implant, for example, for removing or reshaping threads that collect contaminants. Finishing and shaping working surfaces can include surfaces for tap, tap die, plasma spray, burnishing, and thread cleaning. In an embodiment, the screw sharpening or shaping tool can be configured to be attached to an implant drill or implant remover wrench, for in vivo use.

In various embodiments, the instrument is finished to a controlled finished surface that is optimal for the use of the instrument. For example, an instrument for finishing bone for a bone graft can be finished to a roughness that encourages a successful graft (e.g. on the order of 100's of microns) for osteoplastic activity or osteocytes that respond to increased bone roughness. For another example, a finishing tool can be configured to shape an implant surface that is to be biologically clean to a finish that is smoother, for example 1-99 microns. Finishes can allow for the placement of sprayed or painted root conditioners.

It is also expected controlled finishes will enhance wound healing and bone regeneration technology using emerging and new treatments, for example, growth-factor-enhanced matrix (GEM 21S®), a graft material consists of a concentrated solution of pure recombinant human platelet-derived growth factor (rhPDGF-BB), the synthetic form of the body's key natural wound-healing stimulator PDGF-BB, and an osteoconductive (bone scaffold) matrix which is beta-tricalcium phosphate (β-TCP).

One or more embodiments, including those comprising the chemotherapeutic agents applied as described herein, have also shown to be effective on biofilm-contaminated titanium surfaces in the treatment of peri-implant mucositis, peri-implantitis, and in the prevention and early detection of these conditions. Surface decontamination of the implant surface allows for the success of healing by repair or regeneration and for maintenance of supporting structures of the implant. Given the common etiologies of periodontitis and peri-implantitis, the approach to treatment of periodontal and peri-implantitis is similar, and with the more advanced lesions of peri-implantitis, the use of chemotherapeutic agents such as tetracycline and as described herein can help with surface decontamination of the implant surface along with other surgical resective and regenerative techniques.

Embodiments as described herein have been determined to be effective in long term clinical practice, by the prevention of peri-implantitis and especially peri-implant gingivitis with the patient acting as a co-therapist with the use of, for example, 10% carbamide peroxide and site specific oral hygiene delivery applicator instruments as instructed as well as supportive periodontal therapy at pre-determined maintenance appointments at the office. Topical tetracycline is used in pocket sites around implants during treatment with demonstrated bleeding upon probing up to at least 5 mm in depth. Deeper pocket depths associated with implants especially with radiographic evidence of new progressive bone loss are met with follow up appointments and re-evaluations to determine the need for further intervention. Patients can be given instructions to implement treatment protocols at home to act a co-therapist.

Prevention and early detection is the key to successful management of bio-film contaminated implant surface related inflammatory diseases such as peri-implant gingivitis and peri-implantitis.

In an embodiment, the method comprises applying a follow up treatment comprising: administering the solution including 10% carbamide peroxide to a periodontal pocket of a subject; and, or applying or delivering the antibacterial agent consisting essentially of tetracycline to the dental treatment of a subject.

In at least one of the various embodiments, a patient or the patient's caretaker can be instructed to floss with the gel solution including the carbamide peroxide at least once daily for the active phase of the periodontal disease. The subject can also be instructed to apply other topical treatments directly to treatment areas and roots. For example, a subject or caregiver can be instructed to apply topical fluoride paste (e.g. Prevident™) with their finger to a treatment area, as opposed to the manufacturer's suggestion of a toothbrush, which reaches only the upper surface area of the teeth and does not reach to the root. The subject can further be instructed to push or apply topical treatments with various interdental brushes, stimudents and floss. These approaches get the treatment onto and below root surfaces to controlling decay on roots, which has been demonstrated to be caused by different bacteria than the decay on the enamel surfaces of teeth where these treatments are normally applied.

In an embodiment, described is a dental treatment method comprising: providing a gel solution including 10% carbamide peroxide for administration to a treatment area of a subject in conjunction with a dental care treatment that employs anesthetic as a standard of practice, wherein the 10% carbamide peroxide solution anesthetizes the treatment area. The 10% carbamide peroxide gel acts as a mild topical anesthetic which by definition is that form of anesthesia obtained by the direct application of the drug to the mucous membrane surface. For example, in an embodiment, the 10% carbamide peroxide solution has provided a sufficient anesthetic effect for patients without the need for an injectable local anesthetic, where conventionally the dental care treatment required or indicated injectable anesthetic as a standard of practice and/or for patient comfort. One of the most important aspects of the practice of dentistry is the control or elimination of pain. Research demonstrates that more patients stay away from the dental office from fear of pain than from all other reasons combined.

In an embodiment, described is a viscous medicament comprising a part of a gel solution including a peroxide gel; and a part including an antibacterial agent consisting essentially of tetracycline. In an embodiment, described is a viscous medicament comprising a part of a gel solution including 10% carbamide peroxide; and a part including the antibacterial agent consisting essentially of tetracycline. In an embodiment, the medicament is for the treatment of periodontitis. For example, in an embodiment, the medicament is for administering to the periodontal pocket of a subject during the mechanical debridement treatment. In an embodiment, a solution having the peroxide gel, for example the 10% carbamide peroxide, is in a part percentage effective to chemically debride a treatment area for a dental treatment; in an embodiment, the part percentage of the antibacterial agent consisting essentially of tetracycline can be the remaining part of the medicament.

In an embodiment, described is dental product comprising: a dental cleaning device coated or provided with a solution including at least a gel solution including peroxide gel. In an embodiment, the gel solution includes 10% carbamide peroxide. In an embodiment, the dental cleaning device is selected from the group consisting of: brushes and interdental cleaning devices. In an embodiment, the interdental cleaning device is selected from the group consisting of: flosses, picks, or interdental brushes. In an embodiment, the interdental cleaning device is a superfloss including a sponge provided with the at least 10% carbamide peroxide.

In another embodiment, the 10% carbamide peroxide is in a gel solution, or in combination with other antimicrobials in part, applied with an applicator attached to the container holding the specialized gel solution so the applicator is directed into the pocket or area of treatment, for example, the applicator has a tip that is a nozzle, tube, spray nozzle, etc.

In at least one embodiment, described is method for treating oral surgery wounds comprising administering a clinically effective amount tetracycline directly to an oral wound site during treatment. The treatments can comprise procedures such as, for example, bone grafts, surgical membrane placement, connective tissue grafts, extraction sockets, combined periodontal/endodontic lesion treatments, and implant surgical procedures. In at least one embodiment, at least 30-600 mg of pure topical tetracycline, for example tetracycline hydrochloride, can be applied directly to the wound site. In at least one embodiment, the tetracycline can be powder or paste form, or part of a viscous medicament, for example a gel solution. As will be appreciated, as the topical tetracycline is used topically, most of the topical treatment is rinsed away and hence not absorbed into the subject's system.

Examples

As described below, extensive in vivo administration of a viscous tetracycline antibacterial agent and a solution having the 10% carbamide peroxide, for example Gly-Oxide®, together provided enhanced treatment, healing and management of gum disease, including advanced periodontal disease. As will be appreciated, the length of time for treating periodontitis in its maintenance phase be as long as a lifetime, akin to diseases like diabetes. Accordingly, the treatment population included thousands of subjects monitored over thirty years to confirm the efficaciousness of the treatment. Each of the subjects had up to 6 or more recorded pocket sites, which can have up to 32 teeth and other parameters of periodontal disease recordings as well as health recordings in their patient records. The treatment was applied throughout the course of Phase I, Phase II, and Phase III treatments repeatedly without complications (e.g., true allergic reactions). Patients have reported no adverse problems and use these products, mostly daily at home, as part of their oral hygiene regimen. In office complaints to the tetracycline paste were to taste, not pain, and patients rinsed with tap water in a cup and continued with the use of the chemotherapeutic treatment regimen during treatment.

During Phase I treatments of periodontitis, a gel solution including 10% carbamide peroxide was applied directly to the periodontal pocket and pocket areas immediately followed or preceded by 30-600 mg or more of pure topical tetracycline in powder or paste form, also applied directly to the pocket and pocket treatment areas together with the gel solution. The gel solution and the tetracycline was also applied to teeth directly. Tetracycline was added at intervals throughout the treatment. Treatment was performed on pockets from 3 mm up to 10 mm and more.

When pocket tissue was swollen, the 10% carbamide peroxide penetrated the deep pocket under the gum. The 10% carbamide peroxide was in the form of a viscous gel and was applied to the wound site or pocket using a periodontal probe, for example, or using a curet or scaler. For example, one or two drops from a squeeze-bottle applicator was applied to the end of end of a curette tip or scaler, or was applied with a periodontal pocket measuring probe. The peroxide gel was also applied under artificial teeth and implants, for example under restorative bridges such as pontic areas, whether with implants or natural teeth. It was found the peroxide of as little as one or two drops applied to a treatment area as described above was effective as an anesthetic, allowing for deeper mechanical debridement during the procedure without the need for additional anesthetic. Tray application was also unnecessary.

This beneficial effect was enhanced by the use of mechanical debridement tools with optimized cutting edges. For example, sharpening tools that optimize angle of a blade are described U.S. Pat. Nos. 6,074,293, 6,361,408, 6,949,018, U.S. patent application Ser. No. 15/241,252 and International Patent Application PCT/US2015/041998, the entirety of each of which is incorporated by reference hereby. Sharpening the working edges of dental tools, for example curettes and other scalers, prior to treatment reduced even further the need for anesthetics. Sharp refined cutting edges require less torque and pressure on the roots of teeth and less chance of slippage. Mechanical debridement was able to be performed on subjects without other topical anesthetics such as lidocaine or injectable forms of anesthetic (e.g. Novocain), with tool instrument penetration into pockets and instrument wells at well above 5 mm—as much as 7-10 mm and up.

It was found that the treatment, when administered in conjunction with properly sharpened cutting tools, can smooth tooth root surface to 1-5 microns—down to 1 micron. Root conditioning to this degree of smoothness makes the root inhospitable to bacteria and pathogens as the bacteria cannot attach to the root. Thus, the chemical debridement by the gel was able to non-surgically treat pockets at 5 mm and greater, over 10 mm for the instrument well, without surgery. The repeated effort over 4 to 6 months or longer as needed, allows for a progressive reduction in pocket probing depths by epithelial and fibroplastic proliferation and reattachment. Minimal gingival recession was noted as well during the healing period and the long-term Phase III maintenance periods.

It was observed that chemical debridement of the pocket site soft tissue walls with and root surface conditioning with agents such as tetracycline with the viscous peroxide gel allowed for a more rapid and thorough enhanced root planing. Findings included enhanced wound repair with new soft tissue adherence to the root surface and gradual pocket depth reductions with pockets as much as 10 plus millimeters reducing over the course of therapy to as little as 1-3 mm without surgical intervention. Probing pocket depths which, at the start of treatment, seemed hopelessly advanced, were reduced with reductions in tooth mobility and became manageable for limited surgical intervention when needed. Further, the follow up usage of a 10% carbamide peroxide gel by patients at home in accord with treatment guidelines assisted in biofilm control and chemical curettage of the pocket sites to assist in pocket depth reductions for biofilm repopulation control and therefore the clinical, inflammatory disease.

Tetracycline was also applied to the treatment area using a periodontal probe or curet, or in some cases, directly from the capsule or medicine dish into the pocket and surrounding tissue, during mechanical root planning and scaling. The tetracycline was administered as a full-strength powder or paste of pure topical tetracycline. The tetracycline was placed on the curette by wetting the curette cutting edge in sterile saline and placing the wetted curette tip in a plastic medicine cup containing the tetracycline powder, which allowed for the adhesion to the curette tip. For the peroxide gel, a 10% carbamide peroxide gel, just placing the curette into a plastic medicine cup containing the peroxide gel picked up the viscous solution. Other various surgical instruments are used in a similar fashion, for example a periosteal elevator, were used in extraction sites. In the case of the powder, from 30 to 600 mg (milligrams) or more of tetracycline HCL powder was used during the course of a non-surgical treatment depending on the number and severity of the pocketing of the teeth being treated. Careful sterile handling allowed the treating care professional to place the tetracycline in a medicine cup of approximately 20 ml in size but using a much smaller portion of the medicaments. The tetracycline was present in the treatment area for up to 10 minutes or more during mechanical (and chemical) debridement. The tetracycline was not used for irrigation; thus the only dilution was via the subject's crevicular flow and whatever was present of the debriding peroxide solution, which was sufficient to render the tetracycline to a paste-like viscous consistency when applied. As the topical tetracycline was used topically, most of the topical treatment is rinsed away after treatment.

Based on treatment as described herein, tetracycline is believed to help kill the bacteria and soften biofilms consisting of mostly bacteria and condition and help clean the root. During mechanical debridement, a higher pitch ringing sound was audible while working the tooth: the tooth was literally "squeaky clean." The combination of the gel solution including 10% carbamide peroxide and the viscous tetracycline rendered the treatment area, including the root, biologically clean: it is believed the peroxide gel solution and antibacterial agent performs a "chemical curettage" that removes toxins and bacteria that normally adhere and reattach to the root, removes inflamed or diseased tissue, removes foreign pathogens, and removes extraneous and foreign material caught in the teeth such as food particles. As noted above, the tetracycline was not used with irrigation, and was thus in a viscous or paste-like form when added to the pocket at depths of up to 10 mm and over. Biofilm can increase with crevicular flow and more fluid, hence it is believed using tetracycline in a powder, paste or other low aqueous viscous form is beneficial in periodontal treatment and reduces the disease threshold.

It was also found that the subjects did not see visible bleeding during rinsing and tenderness was reduced, even in cases of advanced periodontitis. The glyoxide gel appears to cause lysis of the blood and blood products and inflammatory exudates found in the periodontal pockets and creates a visible "white foam," which patients preferred to see over spitting out visible blood into the dental chair cuspidor when rinsing. Patients reported by the second treatment appointment that their gums do not bleed anymore after following the oral hygiene patient homecare protocol using the 10% carbamide peroxide gel as instructed.

After treatment, healing was evident during the active phase of the disease as subjects had favorable pocket depth reduction through tissue reattachment, repithelialization, fibroblastic reproliferation in the infected site, regrown collagen fibers, new bone growth, pocket depth reduction, and favorable wound healing.

The treatment was repeated a plurality of times during the active phase of the disease. At Phase III maintenance visits, the preferred frequency was every 3 months after the initial active Phase I and Phase II treatment. No true allergic reaction was observed with topical use of the tetracycline or 10% carbamide peroxide gel in the patient population. For instance, tetracycline was used across all office dental treatments, both post-surgical and non-surgical, and used together with peroxide gel or applied separately on different days. When applied to extraction sockets or pockets, patients rarely reported any pain, and there was no swelling and fast healing without morbidity or complications. Motrin® and Tylenol® were the only analgesics used in practice as needed. Subjects also had 90% improvement in arresting bone loss, and in a number of cases, bone regeneration. Patients also saw enhanced gingival repair and comfort and absence of bleeding upon probing and halitosis, for example, among other patient findings. Clinically, one may see also the coronal migration of the epithelial attachment. Patients were routinely treated with high success and tooth retention for a lifetime, with teeth that initially presented with as much as 90% radiographic evidence of bone loss.

Management of tooth mobility in these advanced periodontal bone loss cases consisted of relieving tactile fremitus and centric occlusion prematurities and striving for group function. Minimizing occlusal traumatism whether primary or secondary was helpful in the healing and repair of the periodontium.

Treatments of 10% carbamide peroxide gel and tetracycline were also administered as needed in conjunction with Phase II treatments as described herein, including endodontic-periodontic lesions with simultaneous root canal therapy, extractions, implants, etc.

Treatments of 10% carbamide peroxide gel and tetracycline were also administered in conjunction with the maintenance phase (Phase III) after both non-surgical (Phase I) and surgical treatments (Phase II).

Treatments were applied with the use of mechanical debridement tools with optimized cutting edges, for example, as optimized using sharpening tools as described in U.S. Pat. Nos. 6,074,293, 6,361,408, 6,949,018, U.S. patent application Ser. No. 15/241,252 and International Patent Application PCT/US2015/041998, the entirety of each of which is incorporated by reference hereby.

The oxidation and foaming effect of the carbamide peroxide gel was found to flush dead and living cells, and is believed to help create or maintain an aerobic environment in the periodontium. Carbamide peroxide is not acidic, which is believed to avoid the need for conventional acidic agents that can be used to kill and flush necrotic or unwanted tissue but may also harm the enamel and cementum.

One advantage of the peroxide gel used with the pure, viscous tetracycline is that the debriding is effected with a minimum of aqueous or liquid dilution, which advantageously enhances the treatment effect, resulting in a "chemical curettage" that enhances the mechanical debridement—root planning and scaling—as well as root conditioning and diseased granulation tissue removal in or around the pocket walls. There was little or no visible red blood in their mouth from the inflammation and infected tissues during the enhanced root planing whether during Phase I, Phase II or Phase III treatments using the peroxide gel. It is believed this is due to breaking down of the red blood cells, immunologic inflammatory cell types and blood coagulum from the degenerative epithelial changes in the periodontal pocket wall in chronic destructive periodontitis.

It is believed the tetracycline acts as systemic antibiotic and produces a number of advantageous effects in the periodontium. Intracervicular fluid flow that naturally circulates the viscous tetracycline may improve healing without unduly diluting its antibiotic effect on the treatment area. It is also believed the topical tetracycline also kills bacteria in the pocket, and appears to have fast acting effects, as the pocket wall tissue looks different immediately after use. One conjecture is the tetracycline has a beneficial effect on the tissue proteins, which may account for the advanced healing. It is possible the tetracycline contributes to an aerobic environment hostile to anaerobic pathogens.

It is also believed tetracycline's topical antimicrobial effect when applied as a viscous agent is useful for keeping implants from failing by early recognition and intervention for peri implant diseases. In addition, use of viscous peroxide, for example 10% carbamide peroxide, by the patient as a co-therapist similarly keeps implants from failing. In implant cases, the viscous tetracycline was applied around the implant and "painted" into the pockets forming similar treatments as with periodontitis with treating natural teeth and periodontitis using a periodontal probe, whether at Phase I, Phase II or Phase III.

Other possible beneficial effects of tetracycline are through the demineralization of dentin surfaces, the removal of the smear layer, additional beneficial effects on the cementum, exposing dentinal tubules and reduced tissue destruction which all lead to improved periodontal regeneration.

The invention claimed is:

1. A method of conditioning an implant surface of a diseased dental implant in which the dental implant is within an implant pocket including a tissue surface surrounding the dental implant, comprising:

chemically debriding the implant surface by applying a gel solution including a clinically effective amount of a peroxide and a clinically effective amount of tetracycline directly to the implant surface with a manual dental instrument including a blade having a working edge with a surface roughness of 1 to 5 microns to chemically anesthetize the tissue surface of the implant pocket; and mechanically debriding the implant surface, while performing the step of chemically debriding, by manually scraping the implant surface with the dental instrument such that the peroxide and the tetracycline chemically anesthetize the tissue surface of the implant pocket while the mechanical debridement step is performed, the manual scraping including contacting the implant surface that includes the gel solution directly with the working edge of the blade to finish the implant surface to form an implant surface roughness of 1 to 5 microns.

2. The method of claim 1, wherein the disease of the dental implant is peri-implant mucositis, peri-implant gingivitis, or peri-implantitis.

3. The method of claim 1, wherein the step of applying the gel solution comprises applying the gel solution directly to the working edge of the blade of the dental instrument prior to application to the implant surface.

4. The method of claim 1, further comprising forming the gel solution by mixing a tetracycline powder with a peroxide gel.

5. The method of claim 1, wherein the gel solution is applied a plurality of times to the implant surface while the mechanical debridement is in process.

6. The method of claim 4, wherein prior to forming the gel solution, the tetracycline powder is drawn with a wetted dental instrument to form a paste-like consistency of tetracycline.

7. The method of claim 1, wherein the gel solution comprises at least 10% carbamide peroxide.

8. The method of claim 1, wherein the gel solution is applied to the implant pocket at a depth of 1 to 10 millimeters.

9. The method of claim 1, wherein the dental instrument is selected from the group consisting of a probe, a curette, and a scaler.

10. The method of claim 9, wherein the gel solution is applied directly into the implant pocket with the dental instrument, the dental instrument selected from the group consisting of a periodontal implant probe, a periodontal curette, and a periodontal scaler.

11. The method of claim 1, wherein the blade of the dental instrument includes no deformations and no wire edges.

12. The method of claim 1, further comprising resharpening the working edge of the blade of the dental instrument during debridement to 1 to 5 microns to remove wire edges and deformations formed during debridement to maintain a functional working edge.

13. The method of claim 1, further comprising gumbrushing with the gel solution at least once daily by the subject.

14. The method of claim 13, further comprising flossing with the gel solution at least once daily by the subject.

15. The method of claim 1, wherein the dental implant is a titanium implant.

* * * * *